(12) United States Patent
Kadiyala et al.

(10) Patent No.: US 6,541,024 B1
(45) Date of Patent: Apr. 1, 2003

(54) REGENERATION AND AUGMENTATION OF BONE USING MESENCHYMAL STEM CELLS

(75) Inventors: Sudhakar Kadiyala, Baltimore; Scott P. Bruder, Owings Mills, both of MD (US)

(73) Assignee: Osiris Therapeutics, Inc., Baltimore, MD (US)

( * ) Notice: Subject to any disclaimer, the term of this patent is extended or adjusted under 35 U.S.C. 154(b) by 0 days.

(21) Appl. No.: 09/042,275

(22) Filed: Mar. 13, 1998

Related U.S. Application Data

(63) Continuation-in-part of application No. PCT/US97/06433, filed on Apr. 17, 1997.
(60) Provisional application No. 60/016,245, filed on Apr. 19, 1996, and provisional application No. 60/029,838, filed on Oct. 28, 1996.

(51) Int. Cl.[7] .................................................. A61F 2/28
(52) U.S. Cl. ........................ 424/426; 523/114; 523/115; 623/16
(58) Field of Search .......................... 424/426; 523/114, 523/115; 623/16

(56) References Cited

PUBLICATIONS

Goshima, J. et al., "The Osteogenic Potential of Culture–Expanded Rat Marrow Mesenchymal Cells Assayed In Vivo in Calcium Phosphate Ceramic Blocks," *Clinical Orthopaedics and Related Research*, 262: 298–311 (1991).

Goshima, J. et al. "Osteogenic Potential of Culture–Expanded Rat Marrow Cells as Assayed In Vivo With Porous Calcium Phosphate Ceramic," *Biomaterials*, 12(2):253–258 (1991).

Goshima, J. et al. "The Origin of Bone Formed in Composite Grafts of Porous Calcium Phosphate Ceramic Loaded With Marrow Cells," *Clinical Orthopaedics and Related Research*, 269:274–283 (1991).

Haynesworth, S. et al. "Characterization of Cells with Osteogenic Potential from Human Marrow," *Bone*, 13:81–88 (1992).

Lind, M. et al. "Bone Morphogenetic Protein–2 but not Bone Morphogenetic Protein–4 and –6 Stimulates Chemotactic Migration of Human Osteoblasts, Human Marrow Osteoblasts, and U2–OS Cells," *Bone*, 18(1):53–57 (1996).

Nade, S. et al. "Osteogenesis after Bone and Bone Marrow Transplantation," *Clinical Orthopaedics and Related Research*, 181:255–263 (1983).

Sakata & Takagi, "Effect of Bone Marrow Mononuclear Phagocytes on the Bone Matrix–induced Bone Formation in Rats," *Clinical Orthopaedics and Related Research*, 220:253–258 (1987).

Krzymanski, G. and Wiktor–Jedzejczak, W., "Autologous Bone Marrow–Derived Stromal Fibroblastoid Cells Grown in Vitro for the Treatment of Defects of Mandibular Bones," *Transplantation Proceeding*, 28(6):3528–3530 (1996).

*Primary Examiner*—Carlos A. Azpuru
(74) *Attorney, Agent, or Firm*—Elliot M. Olstein; Raymond J. Lillie

(57) ABSTRACT

Disclosed are compositions and methods for augmenting bone formation by administering isolated human mesenchymal stem cells (hMSCs) with a ceramic material or matrix or by administering hMSCs; fresh, whole marrow; or combinations thereof in a resorbable biopolymer which supports their differentiation into the osteogenic lineage. Contemplated is the delivery of (i) isolated, culture-expanded, human mesenchymal stem cells; (ii) freshly aspirated bone marrow; or (iii) their combination in a carrier material or matrix.

16 Claims, 10 Drawing Sheets

FIG. 1A
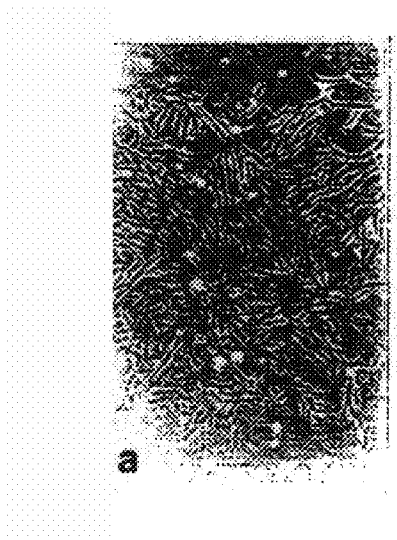
FIG. 1B
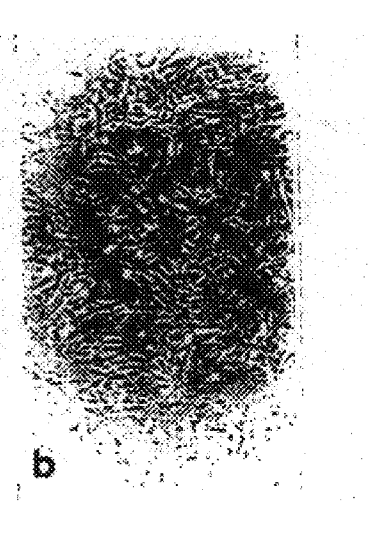
FIG. 1C
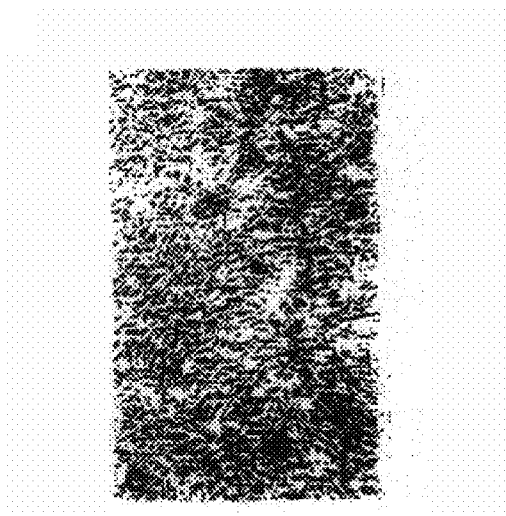
FIG. 1D
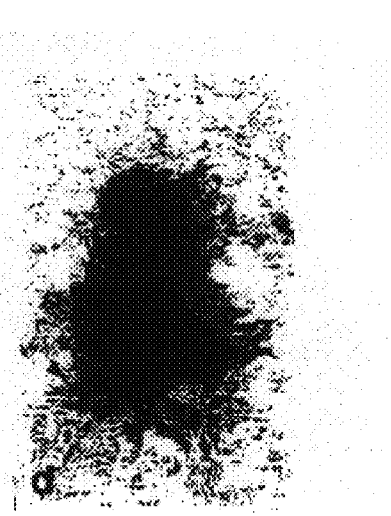
FIG. 2

Marrow-loaded Gelfoam in Canine Femoral Defects at 12 Weeks

Marrow-loaded Gelfoam in Canine Femoral Defects at 16 Weeks

REGENERATION AND AUGMENTATION OF BONE USING MESENCHYMAL STEM CELLS

This application is a continuation-in-part of PCT application no. US97/06433, filed Apr. 17, 1997 (copending) which is a continuation of U.S. provisional application Ser. No. 60/016,245, filed Apr. 19, 1996 and U.S. provisional application Ser. No. 60/029,838 filed Oct. 28, 1996.

Autologous, culture-expanded, bone marrow-derived MSCs have now been shown to regenerate clinically significant bone defects. Using techniques for isolating and cultivating human MSCs, it should be possible to implement therapeutic strategies based on the administration of a patient's own cells which have been harvested by a simple iliac crest aspiration. This method may provide an alternative to autogenous bone grafting, and will be particularly useful in clinical settings such as ageing and osteoporosis, where the number and/or function of endogenous MSCs have been reduced.

The repair of large segmental defects in diaphyseal bone is a significant problem faced by orthopaedic surgeons. Although such bone loss may occur as the result of acute injury, these massive defects commonly present secondary to congenital malformations, benign and malignant tumors, osseous infection, and fracture non-union. The use of fresh autologous bone graft material has been viewed as the historical standard of treatment but is associated with substantial morbidity including infection, malformation, pain, and loss of function (28). The complications resulting from graft harvest, combined with its limited supply, have inspired the development of alternative strategies for the repair of clinically significant bone defects. The primary approach to this problem has focused on the development of effective bone implant materials.

Three general classes of bone implants have emerged from these investigational efforts, and these classes may be categorized as osteoconductive, osteoinductive, or directly osteogenic. Allograft bone is probably the best known type of osteoconductive implant. Although widely used for many years, the risk of disease transmission, host rejection, and lack of osteoinduction compromise its desirability (31). Synthetic osteoconductive implants include titanium fibermetals and ceramics composed of hydroxyapatite and/or tricalcium phosphate. The favorably porous nature of these implants facilitate bony ingrowth, but their lack of osteoinductive potential limits their utility. A variety of osteoinductive compounds have also been studied, including demineralized bone matrix, which is known to contain bone morphogenic proteins (BMP). Since Urist's original discovery of BMP, others have characterized, cloned, expressed, and implanted purified or recombinant BMPs in orthotopic sites for the repair of large bone defects (13,50,57). The success of this approach has hinged on the presence of mesenchymal cells capable of responding to the inductive signal provided by the BMP (29). It is these mesenchymal progenitors which undergo osteogenic differentiation and are ultimately responsible for synthesizing new bone at the surgical site.

One alternative to the osteoinductive approach is the implantation of living cells which are directly osteogenic. Since bone marrow has been shown to contain a population of cells which possess osteogenic potential, some have devised experimental therapies based on the implantation of fresh autologous or syngeneic marrow at sites in need of skeletal repair (15,55,56). Though sound in principle, the practicality of obtaining enough bone marrow with the requisite number of osteoprogenitor cells is limiting.

SUMMARY OF THE INVENTION

The present invention provides compositions and methods for directing MSCs cultivated in vitro to differentiate into specific cell lineage pathways prior to, at the time of or following, their implantation for the therapeutic treatment of elective procedures or pathologic conditions in humans and other species. The use of both autologous and allogenic MSCs is contemplated in this invention.

The investigations reported here confirm the in vitro and in vivo osteogenic potential of MSCs; demonstrate the in vivo osteogenic potential of MSCs when implanted at an ectopic subcutaneous site; and illustrate that purified, culture-expanded MSCs can regenerate a segmental bone defect which would otherwise result in a clinical non-union. These experiments compared the healing potential of MSCs delivered in an osteoconductive or other appropriate resorbable medium. We also contemplate de novo formation of bone at the site of a desired fusion, e.g. spinal or other joint fusions.

The invention provides a method for augmenting bone formation in an individual in need thereof by administering isolated human mesenchymal stem cells with a matrix which supports the differentiation of such stem cells into the osteogenic lineage to an extent sufficient to generate bone formation therefrom. The matrix is preferably selected from a ceramic and a resorbable biopolymer. The ceramic can be in particulate form or can be in the form of a structurally stable, three dimensional implant. The structurally stable, three dimensional implant can be, for example, a cube, cylinder, block or an appropriate anatomical form. The resorbable biopolymer is a gelatin, collagen or cellulose matrix, can be in the form of a powder or sponge, and is preferably a porcine skin-derived gelatin.

Particularly, the invention provides a method for effecting the repair or regeneration of bone defects in an animal or individual in need thereof. Such defects include, for example, segmental bone defects, non-unions, malunions or delayed unions, cysts, tumors, necroses or developmental abnormalities. Other conditions requiring bone augmentation, such as joint reconstruction, cosmetic reconstruction or bone fusion, such as spinal fusion or joint fusion, are treated in an individual by administering, for example into the site of bone in need of augmentation, fresh whole marrow and/or isolated human mesenchymal stem cells or combinations thereof in the gelatin, cellulose or collagen based medium to an extent sufficient to augment bone formation therefrom. The composition can also contain one or more other components which degrade, resorb or remodel at rates approximating the formation of new tissue.

The invention also contemplates the use of other extracellular matrix components, along with the cells, so as to achieve osteoconduction or osteoinduction. In addition, by varying the ratios of the components in said biodegradable matrices, surgical handling properties of the cell-biomatrix implants can be adjusted in a range from a dimensionally stable matrix, such as a sponge or film, to a powder.

The above method can further comprise administering to the individual at least one bioactive factor which induces or accelerates the differentiation of mesenchymal stem cells into the osteogenic lineage. The MSCs can be contacted with the bioactive factor ex vivo and are preferably contacted with the bioactive factor when the MSCs are in contact with the matrix. The bioactive factor can be, for example, a synthetic glucocorticoid, such as dexamethasone, or a bone morphogenic protein, such as BMP-2, BMP-3, BMP-4, BMP-6 or BMP-7. The bone morphogenic protein can be in a liquid or semi-solid carrier suitable for intramuscular, intravenous, intramedullary or intra-articular injection.

The invention further provides a composition for augmenting bone formation, which composition comprises a matrix selected from the group consisting of absorbable gelatin, cellulose and collagen in combination with at least one of fresh bone marrow and/or isolated mesenchymal stem cells. The composition can be used in the form of a sponge, strip, powder, gel or web. The invention also provides a method for augmenting bone formation in an individual in need thereof by administering to said individual a bone formation augmenting amount of the composition.

More particularly, the invention provides a method for effecting the repair of segmental bone defects, non-unions, malunions or delayed unions in an individual in need thereof by administering into the bone defect of said person isolated human mesenchymal stem cells in a porous ceramic carrier, thereby inducing the differentiation of such stem cells into the osteogenic lineage to an extent sufficient to generate bone formation therefrom. Preferably, the porous ceramic carrier comprises hydroxyapatite and, more preferably, the porous ceramic carrier further comprises β-tricalcium phosphate. The porous ceramic carrier may also contain one or more other biodegradable carrier components which degrade, resorb or remodel at rates approximating the formation of new tissue extracellular matrix or normal bone turnover.

The invention also provides for the use of other extracellular matrix components, or other constituents, so as to achieve osteoconductive or osteoinductive properties similar to natural extracellular matrix. The composition is an absorbable gelatin, cellulose and/or collagen-based matrix in combination with bone marrow and/or isolated mesenchymal stem cells. The composition can be used in the form of a sponge, strip, powder, gel, web or other physical format. The composition is, for example, inserted in the defect and results in osteogenic healing of the defect.

In addition, by varying the ratios of the components in said biodegradable matrices, surgical handling properties of the cell-biomatrix implants can be adjusted in a range from a porous ceramic block or a moldable, putty-like consistency to a pliable gel or slurry.

More particularly, the invention comprises a rigid cell-matrix implant for large segmental defects, spinal fusions or non-unions, gel or slurry cell-matrix implants, or infusions for stabilized fractures and other segmental bone defects. Custom cell-matrix implants containing autologous or allogeneic MSCs can be administered using open or arthroscopic surgical techniques or percutaneous insertion, e.g. direct injection, cannulation or catheterization.

In a preferred embodiment, a composition of human mesenchymal stem cells (hMSCs) is obtained from either homogeneous, culture-expanded preparations derived from whole-marrow (or other pre-natal or post-natal source of autologous or allogeneic hMSCs), or from enriched or heterogenous cultures containing an effective dose of hMSCs. The key to effective clinical outcomes using MSC therapy is to provide that number of mesenchymal stem cells to the patient which repairs the bone or other tissue defect. This is referred to as the "Regenerative MSC Threshold", or that concentration of MSCs necessary to achieve direct repair of the tissue defect. The Regenerative MSC Threshold will vary by: 1) type of tissue (i.e., bone, cartilage, ligament, tendon, muscle, marrow stroma, dermis and other connective tissue); 2) size or extent of tissue defect; 3) formulation with pharmaceutical carrier; and 4) age of the patient. In a complete medium or chemically defined serum-free medium, isolated, culture-expanded hMSCs are capable of augmenting bone formation.

In another aspect the invention contemplates the delivery of (i) isolated, culture-expanded, human mesenchymal stem cells; (ii) freshly aspirated bone marrow; or (iii) their combination in a carrier material or matrix to provide for improved bone fusion area and fusion mass, when compared to the matrix alone.

One composition of the invention is envisioned as a combination of materials implanted in order to effect bone repair, osseous fusion, or bone augmentation. The components of this implanted material include, in part, porous granular ceramic, ranging in size from 0.5 mm to 4 mm in diameter, with a preferred size ranging from 1.0 to 2.5 mm in diameter. The composition of the ceramic may range from 100% hydroxyapatite to 100% tricalcium phosphate, and in the preferred form, consists of a 60/40 mixture of hydroxyapatite and tricalcium phosphate. The ceramic material may be uncoated, or coated with a variety of materials including autologous serum, purified fibronectin, purified laminin, or other molecules that support cell adhesion. The granular ceramic material can be combined with MSCs ranging in a concentration of at least 10 thousand, more generally at least 100 thousand and more preferably at least 1 and up to at least 3 million cells per cc. In general, the cells do not exceed 30 million cells and more generally do not exceed 10 million cells with the cells in most cases not exceeding 3 million up to no more than 15 million cells per cc. It is also envisioned that the cells may be in the form of fresh marrow obtained intraoperatively, without ex vivo culture-expansion.

Bone marrow cells may be obtained from iliac crest, femora, tibiae, spine, rib or other medullary spaces. Other sources of human mesenchymal stem cells include embryonic yolk sac, placenta, umbilical cord, periosteum, fetal and adolescent skin, and blood. The cells are incubated at 37° C. with the ceramic for 0 to 5 hours, preferably 3 hours. Prior to implant, the cell-loaded granules can be combined with either fresh peripheral blood, human fibrin, fresh bone marrow, obtained by routine aspiration, or other biological adjuvant. These final combinations are allowed to form a soft blood clot which helps to keep the material together at the graft site. Implant or delivery methods include open or arthroscopic surgery and direct implant by injection, e.g. syringe or cannula. Finally, these implants may be used in the presence or absence of fixation devices, which themselves may be internally or externally placed and secured.

The composition can also contain additional components, such as osteoinductive factors. Such osteoinductive factors include, for example, dexamethasone, ascorbic acid-2-phosphate, β-glycerophosphate and TGF-β superfamily proteins, such as the bone morphogenic proteins (BMPs). The composition can also contain antibiotic, antimycotic, antiinflammatory, immunosuppressive and other types of therapeutic, preservative and excipient agents.

BRIEF DESCRIPTION OF THE DRAWINGS

FIGS. 1A–1D. Phase contrast photomicrographs of rat MSC cultures at various stages of development.

FIG. 1A. A MSC colony at day seven of primary culture is composed of uniformly spindle-shaped cells.

FIG. 1B. Passage one rat MSCs are distributed evenly across the surface of the dish 4 days after replating.

FIG. 1C. Rat MSCs grown in Control Medium for twenty-eight days become confluent and multi-layered, but do not form mineralized nodules. APase staining (dark gray) reveals a fraction of cells which are positive.

FIG. 1D. Rat MSC cultures grown in the presence of Osteogenic Supplements for twenty-eight days form mineralized nodules which stain black by the von Kossa method. Cell cultures were stained by APase and von Kossa histochemical techniques as described below (Unstained (a,b), Alkaline phosphatase histochemistry and von Kossa (c,d), all x45).

FIG. 2. Light micrograph of a representative histological section from a MSC-loaded HA/TCP implant placed ectopically in subcutaneous tissue. MSCs were loaded and the sample was implanted as described below, harvested at eight weeks, decalcified, and processed in paraffin for microscopy. Only remnants of the HA/TCP ceramic (c) remain, while the pores of the implant are filled with bone (b), blood vessels (v), and hematopoietic elements including adipocytes (Toluidine blue-O, x70).

FIGS. 3A and 3B. Defects left empty;

FIGS. 3C and 3D. Defects fitted with HA/TCP carrier alone;

FIGS. 3E and 3F. Defects fitted with a MSC-loaded HA/TCP carrier;

FIGS. 3G and 3H. Defects fitted with a marrow-loaded HA/TCP carrier. Defects left empty following segmental gap resection undergo reactive bone formation at the cut ends of the bone, leading to a classical non-union in this well established model. At four weeks, the MSC-loaded samples have begun to fill the pores of the implant material. No union is evident in any implant type at four weeks. By eight weeks, modest union of the host-implant interface has occurred in the carrier (d) and carrier plus marrow groups (h), but complete integration and bone bridging is evident in the carrier plus MSC group (f). Total filling of the pores with bone in the MSC-loaded sample is also evident in panel F. (x1.5)

FIGS. 4A and 4B. Defects fitted with HA/TCP carrier alone at four and eight weeks, respectively;

FIGS. 4C and 4D. Defects fitted with a MSC-loaded HA/TCP carrier at four and eight weeks, respectively;

FIGS. 4E and 4F. Defects fitted with a marrow-loaded HA/TCP at four and eight weeks, respectively. New bone present within the pores, or at the host-implant interface appears blue or violet in these specimens. Importantly, only samples containing a MSC-loaded implant effectively heal the defect, as noted by the substantial amount of bone present within the implant and at the interface with the host in panels c and d. See text for further details (Toluidine blue-O, x8).

FIG. 6. Osteogenic differentiation of human MSCs in vitro. Phase contrast photomicrographs (a, b) of human MSC cultures under growth and osteogenic conditions.

DETAILED DESCRIPTION OF THE INVENTION

Figure 3A:
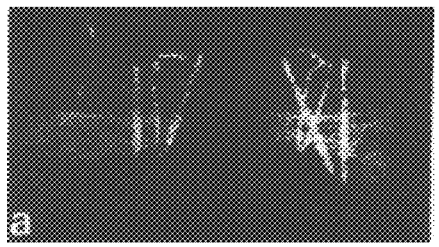
FIGS. 3A–3H. High resolution radiographs showing the healing of the segmental defect at four and eight weeks with various implants. The radiographs were obtained on a Faxitron imaging system immediately following sacrifice. The polyethylene fixation plate is on the top of the bone in each radiograph. The four week radiograph is on the left, and the eight week radiograph is on the right for each group. The radiodensity of the HA/TCP material reveals the porous nature and the central canal of each implant.

Bone grafting procedures are widely used to treat acute fractures, fracture non-unions, bone defects, and to achieve therapeutic arthrodesis. Autogenous cancellous bone is the current "gold standard" for clinical bone grafting. Contemporary dogma attributes this effectiveness to three primary intrinsic properties: osteoconduction, osteogenic cells, and osteoinduction.

The marrow or isolated mesenchymal stem cells can be autologous, allogeneic or from xenogeneic sources, and can be embryonic or from post-natal sources. Bone marrow cells may be obtained from iliac crest, femora, tibiae, spine, rib or other medullary spaces. Other sources of human mesenchymal stem cells include embryonic yolk sac, placenta, umbilical cord, periosteum, fetal and adolescent skin, and blood. In order to obtain mesenchymal stem cells, it is necessary to isolate rare pluripotent mesenchymal stem cells from other cells in the bone marrow or other MSC source.

The present invention provides a composition for the repair of bone defects by the rapid regeneration of healthy bone. The composition is an absorbable gelatin, cellulose and/or collagen-based matrix in combination with bone marrow and/or isolated mesenchymal stem cells. The composition can be used in the form of a sponge, strip, powder, gel, web or other physical format. The composition is, for example, inserted in the defect and results in osteogenic healing of the defect.

The composition can also contain additional components, such as osteoinductive factors. Such osteoinductive factors include, for example, dexamethasone, ascorbic acid-2-phosphate, β-glycerophosphate and TGF-β superfamily proteins, such as the bone morphogenic proteins (BMPs). The composition can also contain antibiotic, antimycotic, antiinflammatory, immunosuppressive and other types of therapeutic, preservative and excipient agents.

The invention also provides a method for treating a bone defect in an animal, particularly a mammal and even more particularly a human, in need thereof which comprises administering to the bone defect of said animal a bone defect-regenerative amount of the composition of the invention.

The investigations reported here confirm the in vivo healing potential of fresh whole marrow or MSCs delivered in the matrix alone.

The invention also contemplates the use of other extracellular matrix components, along with the cells, so as to achieve osteoconductive or osteoinductive properties. In addition, by varying the ratios of the components in said biodegradable matrices, surgical handling properties of the cell-biomatrix implants can be adjusted in a range from a dimensionally stable matrix, such as a sponge or film, to a moldable, putty-like consistency to a pliable gel or slurry to a powder.

In a particularly preferred embodiment, the composition of the invention comprises an absorbable implant, containing whole marrow and/or isolated MSCs for repair of segmental defects, spinal fusions or non-unions and other bone defects. Custom cell-matrix implants containing autologous, allogeneic or xenogeneic bone marrow and/or MSCs can be administered using open surgical techniques, arthroscopic techniques or percutaneous injection.

Human mesenchymal stem cells (hMSCs) can be provided as either homogeneous, culture-expanded preparations derived from whole-marrow (or other pre-natal or post-natal source of autologous or allogeneic hMSCs), from hMSC-enriched or heterogenous cultures containing an effective dose of at least about $10^3$ and preferably at least about $10^5$, preferably about $10^4$ or up to $10^6$, MSCs per milliliter of the composition. The key to effective clinical outcomes, in this embodiment using MSC therapy, is to provide that number of enriched or culture-expanded mesenchymal stem cells to the patient, or about the same number in an optimized medium, which repairs the bone or other tissue defect beyond that in a volume of whole marrow equivalent to that of the defect. This is referred to as the "Regenerative MSC Threshold", or that concentration of MSCs necessary to achieve direct repair of the tissue defect. The Regenerative MSC Threshold will vary by: 1) type of tissue (i.e., bone, cartilage, ligament, tendon, muscle, marrow stroma, dermis and other connective tissue); 2) size or extent of tissue defect; 3) formulation with pharmaceutical carrier; and 4) age of the patient.

In a preferred embodiment, the method further comprises administering at least one bioactive factor which further induces or accelerates the differentiation of such mesenchymal stem cells into the osteogenic lineage. Preferably, the cells are contacted with the bioactive factor ex vivo, while in the matrix, or injected into the defect site at or following the implantation of the composition of the invention. It is particularly preferred that the bioactive factor is a member of the TGF-β superfamily comprising various tissue growth factors, particularly bone morphogenic proteins, such as at least one selected from the group consisting of BMP-2, BMP-3, BMP-4, BMP-6 and BMP-7.

In the embodiment which uses a gelatin-based matrix, an appropriate absorbable gelatin sponge, powder or film is cross-linked gelatin, for example, Gelfoam® (Upjohn, Inc., Kalamazoo, Mich.) which is formed from denatured collagen. The absorbable gelatin-based matrix can be combined with the bone reparative cells and, optionally, other active ingredients by soaking the absorbable gelatin sponge in a cell suspension of the bone marrow and/or MSC cells, where the suspension liquid can have other active ingredients dissolved therein. Alternately, a predetermined amount of a cell suspension can be transferred on top of the gelatin sponge, and the cell suspension can be absorbed.

In the embodiment which uses a cellulose-based matrix, an appropriate absorbable cellulose is regenerated oxidized cellulose sheet material, for example, Surgicel® (Johnson & Johnson, New Brunswick, N.J.) which is available in the form of various sized strips or Oxycel® (Becton Dickinson, Franklin Lakes, N.J.) which is available in the form of various sized pads, pledgets and strips. The absorbable cellulose-based matrix can be combined with the bone reparative cells and, optionally, other active ingredients by soaking the absorbable cellulose-based matrix in a cell suspension of the bone marrow and/or MSC cells, where the suspension liquid can have other active ingredients dissolved therein. Alternately, a predetermined amount of a cell suspension can be transferred on top of the cellulose-based matrix, and the cell suspension can be absorbed.

In the embodiment which uses a collagen-based matrix, an appropriate resorbable collagen is purified bovine corium collagen, for example, Avitene® (MedChem, Woburn, Mass.) which is available in various sizes of nonwoven web and fibrous foam, Helistat® (Marion Merrell Dow, Kansas City, Mo.) which is available in various size sponges or Hemotene® (Astra, Westborough, Mass.) which is available in powder form. The resorbable collagen-based matrix can be combined with the bone reparative cells and, optionally, other active ingredients by soaking the resorbable collagen-based matrix in a cell suspension of the bone marrow and/or MSC cells, where the suspension liquid can have other active ingredients dissolved therein. Alternately, a predetermined amount of a cell suspension can be transferred on top of the collagen-based matrix, and the cell suspension can be absorbed.

The above gelatin-based, cellulose-based and collagen-based matrices may, optionally, possess hemostatic properties.

Preferred active ingredients are those biological agents which enhance wound healing or regeneration of bone, particularly recombinant proteins. Such active ingredients are present in an amount sufficient to enhance healing of a wound, i.e., a wound healing-effective amount. The actual amount of the active ingredient will be determined by the attending clinician and will depend on various factors such as the severity of the wound, the condition of the patient, the age of the patient and any collateral injuries or medical ailments possessed by the patient. Generally, the amount of active ingredient will be in the range of about 1 pg/cm$^3$ to 5 mg/cm$^3$.

EXAMPLE 1

Rat Gap Defect Repair

Materials & Methods

Materials

Dexamethasone (Dex), sodium β-glycerophosphate (βGP), antibiotic penicillin/streptomycin, and alkaline phosphatase histochemistry kit #85 were purchased from Sigma Chemical Co. (St. Louis, Mo.), DMEM-LG (DMEM) tissue culture medium from GIBCO Laboratories (Grand Island, N.Y.), and L-ascorbic acid-2-phosphate (AsAP) from Wako Chemical (Osaka, Japan). Fetal bovine serum (FBS) was purchased from GIBCO following an extensive testing and selection protocol (35). Porous hydroxyapatite/β-tricalcium phosphate (HA/TCP) ceramic, mean pore size 200–450 μm, was generously provided by Zimmer, Inc. (Warsaw, Ind.). All other routine reagents used were of analytical grade.

MSC Isolation and Cultivation

MSC isolation and culture expansion was performed according to previously published methods. Briefly, male Fisher F344 rats (200–275 g) were sacrificed by pentobarbital overdose. The tibias and the femurs were recovered by dissection under sterile conditions, the metaphyseal ends of the bones were cut, and the marrow plugs were flushed out by passing saline through a needle inserted into one end of the bone. Pooled marrow clots were dispersed by gentle pipetting, followed by sequential passage through a series of smaller needles yielding a single-cell suspension. The cells were then centrifuged for ten minutes at 900×g, and resuspended in DMEM containing 10% FBS (Control Medium). Fifty million nucleated cells were plated onto petri-dishes (sixty cm$^2$) in seven milliliters of Control Medium, and grown at 37° C. in the presence of 5% $CO_2$. Non-adherent cells were removed at the time of the first medium change, four days post plating, and cells were routinely fed twice weekly thereafter. These primary cultures approached confluence typically at thirteen days, were then released by a five minute exposure to 0.25% trypsin containing one millimolar EDTA, and subcultivated at a density of 10$^4$ cells/cm$^2$. Cells for implantation were derived from these first passage cultures ten days after replating, at which time they were approximately 85% confluent.

In Vitro Osteogenic Assays

At the end of first passage, MSCs were replated into six-well plates at a density of 10$^4$ cells/cm$^2$ in Control Medium. The following day (Day 0), fresh Control Medium was provided, and the cells were grown in the absence or presence of Osteogenic Supplements (OS) (100 nanomolar Dex, 0.05 millimolar AsAP and ten millimolar β-GP) (23). Media changes were performed twice weekly, and at days seven, fourteen, twenty-one, and twenty-eight, cultures were assayed for cell number, alkaline phosphatase (APase) histochemistry, and mineralized matrix production utilizing techniques previously described (23).

Implant Preparation

HA/TCP blocks were shaped into cylinders approximately four millimeter in diameter and eight millimeter in length. A central canal roughly one millimeter in diameter was bored through the length of the entire cylinder using an eighteen gauge hypodermic needle. Cylinders were cleaned by sonication and rinsing in distilled water, and then sterilized by 220° C. dry heat for five hours. The cylinders were subsequently coated with human plasma fibronectin (CalBiochem, Irvine, Calif.) by soaking in a 100 microgram per milliliter solution for sixteen hours at 4° C. The implants were then air dried at room temperature overnight in a sterile biosafety cabinet, and stored at 4° C. HA/TCP cubes, measuring three millimeter per side, were similarly prepared and coated with fibronectin as described above for use in the ectopic osteogenesis assay.

HA/TCP implants, both in cube and cylinder form, were loaded with MSCs using a modification of a technique previously described (37). Briefly, implants were placed in a suspension of MSCs (7.5×10$^6$ cells/ml) in serum free DMEM. The loading vessel was capped, and the implants were subjected to a vacuum in three bursts of five seconds each to remove air present within the pores of the HA/TCP, and to facilitate fluid flow into the pores. The loading vessels were capped loosely, placed in a tissue culture incubator for two hours, and gently agitated every thirty minutes until the time of surgery. Cell-free control cylinders were treated identically, with the notable exception that the serum free DMEM contained no cells. The third implant group was designed to generously approximate the clinically relevant control of a fresh bone marrow aspirate. Just prior to implantation, fresh marrow cell suspensions were obtained as previously described, centrifuged for ten minutes at 900×g, and resuspended in a volume of serum free DMEM which would coat each cylinder with the number of bone marrow cells derived from one entire femur, approximately fifty million (55,56). The HA/TCP implants were loaded with this fresh marrow by rolling them in the congealed marrow suspension.

Surgical Model and Experimental Design

The rat femoral gap model described here is a modification of one used extensively to study long bone repair (12,21,37,50,55,56). Briefly, both femurs of male F344 rats (300–350 g) were exposed by an anterolateral approach. Soft tissue and muscle was elevated while keeping the periosteum intact along the surface of the bone. A polyethylene fixation plate (four by four by twenty-three millimeters) (Hospital for Special Surgery, New York, N.Y.) was secured to the anterolateral aspect of each femur by four threaded Kirschner-wires and two cerclage wires (Zimmer, Warsaw, Ind.). An eight millimeter transverse segment of the central diaphysis, along with its adherent periosteum, was removed by a rotary osteotomy burr under saline irrigation. These stabilized segmental defects were either left empty, or replaced with a cell-free HA/TCP cylinder, a MSC-loaded cylinder, or a cylinder loaded with a fresh marrow cell suspension. Implants were secured by placing two 4-0 Vicryl (Ethicon, Somerville, N.J.) sutures around the ceramic and the fixation plate. The muscles were apposed, and the fascia and skin were closed in a routine layered fashion. Rats implanted with MSC-loaded cylinders also received subcutaneous implants of the MSC-loaded HA/TCP cubes to correlate the ectopic osteogenesis assay with orthotopic bone regeneration and the in vitro osteogenic potential of syngeneic MSCs. Rats implanted with marrow-loaded cylinders similarly received subcutaneous implants of marrow-loaded cubes. The animals were allowed full activity in their cages post-operatively. No animals experienced failure of fixation or other post-operative complications. At least six limbs were used for each of the implant groups, randomly selected between left or right. Upon sacrifice at four and eight weeks, the vascular tree of some animals was perfused with India ink, and the entire femur and surrounding soft tissue was carefully dissected. Specimens were immediately evaluated radiographically, and subsequently processed for undecalcified histology.

Radiographic Analysis

The specimens were radiographed using a high resolution Faxitron Imaging system (Buffalo Grove, Ill.) with an exposure of thirty-five kVP for thirty seconds. The radiographs were independently evaluated by two of the authors who were blinded with respect to the duration and type of implant. Bone formation was scored on a semiquantitative scale with ranges as follows: distal host-implant union (0–2); proximal host-implant union (0–2); and implant core density (0–4). The union scores and the core density scores were added to give a maximum possible score of eight for each implant. Results from both examiners were averaged to give final scores.

Histology and Histomorphometry

Following fixation in 10% buffered formalin, the femurs were dehydrated, cleared, and embedded in polymethylmethacrylate. Longitudinal sections were cut on a water-cooled Isomet saw (Buehler, Wis.), and a central section of each leg was ground to 100 micrometer thickness, polished, and stained with Toluidine blue-O. Leica Quantimet 500MC (Cambridge, UK) image analysis software was used to determine the area of HA/TCP implant, bone, and soft tissue in the diaphyseal defect region of each section. The data were analyzed by one-way analysis of variance (ANOVA) (Sigmastat, Jandel Scientific). Further analyses were performed according to post hoc Student-Newman-Keuls tests. Subcutaneously implanted ceramic cubes were similarly fixed in formalin, then decalcified, dehydrated, embedded in paraffin, serially sectioned, and stained with Toluidine blue-O.

Results

MSC Cultivation and Osteogenic Differentiation in vitro

Rat MSC cultures were established from syngeneic animals and, by seven days, formed characteristic colonies on the surface of the culture dish (FIG. 1A). Several hundred MSC colonies arose from the fifty million nucleated cells seeded on each sixty $cm^2$ dish. On the basis of this observation, rat MSCs, like human MSCs (3,19), appear to be present at a frequency of approximately one in $10^5$ nucleated marrow cells. Primary MSC cultures subcultivated on day fourteen attached uniformly to the surface of new dishes, and were allowed to divide for roughly ten days, or until the dishes became ~85% confluent. Passaged cells also demonstrate a characteristic morphology (FIG. 1B), and uniformly divide upon the dish resulting in an even distribution of MSCs throughout the plate. Cells derived from this first passage were used for preparing implants as described above, and an aliquot was used to confirm the in vitro osteogenic potential of rat MSCs.

Seven days after replating for the osteogenic assay, both Control and OS-treated cultures were composed of spindle-shaped cells, 40–50% of which were stained for APase. During the next twenty-one days, Control cells remained fibroblastic, increased their cell surface APase, but never underwent the morphologic changes associated with the development of mineralized bone nodules (FIG. 1C). By contrast, OS-treated cultures began to form aggregates of polygonal and cuboidal cells intensely stained for APase, and by day twenty-one, the cultures had formed characteristic bone-like nodules which contained von Kossa stained mineral deposits. Further mineralization of these nodules through day twenty-eight (FIG. 1D) was accompanied by a decrease in APase staining, especially within the internodular regions.

MSC-Mediated Osteogenesis in Ectopic HA/TCP Implants

All MSC-loaded HA/TCP cubes implanted in the host rats had ample evidence of osteogenesis by four weeks. At the eight week time point, a substantial amount of bone, and occasionally cartilage, was present within the pores of the cubes. A representative section from a MSC-loaded cube harvested eight weeks following implantation is shown in FIG. 2. The unstained granular areas reflect the former regions of ceramic material which have been removed during the decalcification step of specimen preparation. As seen in the photomicrograph, bone formation occurs within the pores of the cubes, and is associated with vascular elements which penetrate the implant. Such angiogenesis is obligatory to new bone formation since the secretory activity of osteoblasts is an oriented phenomenon guided by vasculature. Both woven and lamellar bone can be seen depending on the duration of implantation, and the precise region examined. Most of the pores are filled with bone and small islands of hematopoietic elements, with the remainder being filled with a loose connective tissue. In contrast to these MSC-loaded samples, cubes loaded with fresh marrow contained negligible osseous tissue at four weeks, and only slightly more even at eight weeks. As previously demonstrated (19), cubes implanted without MSCs or marrow contained no bone, but were filled with fibrous tissue and blood vessels.

Radiographic Evaluation

Figure 3B:
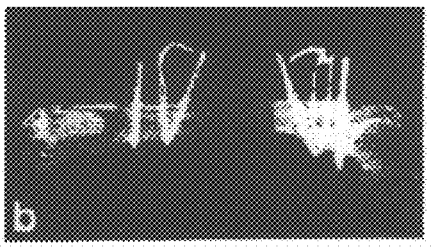
Figure 3C:
Figure 3D:
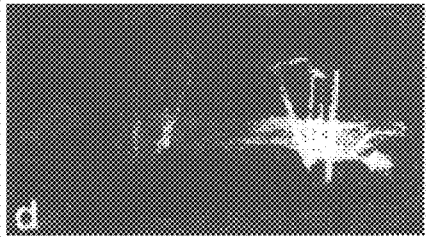

High resolution Faxitron radiographs provided sufficient clarity and detail to discern subtle changes occurring within the implant and the surrounding host bone. FIG. 3 shows representative radiographs of the femurs from each of the groups recovered at four and eight weeks post-implantation. As demonstrated in these radiographs, the fixation remained intact in all the samples and there were no fractures in any of the femurs. In animals whose femoral defects were left empty, reactive bone formation at the transversely cut edges of the host femur was observed at four weeks (FIG. 3A). By eight weeks, slightly more bone was present within the gap, however, most of this bone appeared to form along the edge of the fixation plate which was in contact with the periosteum (FIG. 3B). Every specimen which was left empty resulted in the formation of a radiographic non-union. Some limbs, irrespective of the group, also contained an eccentric spicule of bone which was usually on the outside of the defect opposite the fixation plate.

Figure 3E:
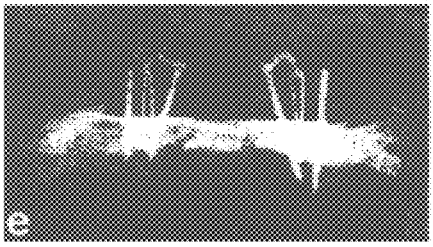
Figure 3F:
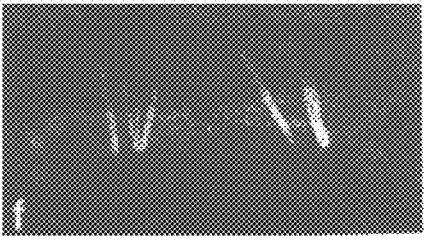
Figure 3G:
Figure 3H:

When the HA/TCP cylinder was implanted, negligible reactive bone formation occurred at the cut edges of the femur. Due to the mineral content of the implant material (HA/TCP), one can appreciate the structural details of the implant itself upon radiographic evaluation. The details of the central canal and pores are clearly visible in the four week radiographs (FIG. 3C), and serve to provide an important baseline for comparison to the other radiographic images. Blurring of the pore margins can be appreciated by eight weeks (FIG. 3D) in these cell-free implants. Importantly, the lack of union between the implant and the host is manifested as a clear zone of radiolucency between the implant itself and the cut edges of the femur in all animals at four weeks. In contrast to the four week carrier alone, animals which received MSC-loaded HA/TCP cylinders demonstrated substantial new bone formation within the pores of the implant by four weeks (FIG. 3E). Increasing radiodensity, and obliteration of the apparent pore structure, was used as an indication of new bone formation within the core of the implant. Although integration of the implant, or union, was not observed by four weeks, the subsequent formation of a radiodense bone bridge between the implant and the host completely masked the interface. By eight weeks, the MSC-loaded implant was contiguous and completely integrated with the normal host bone (FIG. 3F). HA/TCP implants which were loaded with fresh marrow did not appear to produce radiodense bone within the pores at either time point, although modest integration with the cut ends of the host bone was evident by eight weeks (FIGS. 3G and 3H).

The average of the radiographic scores at each time point for each implant group is provided in Table 1.

TABLE 1

Average of Radiographic Scores for Each Implant Group

|  | Four Weeks | | | Eight Weeks | | |
| --- | --- | --- | --- | --- | --- | --- |
|  | C only | C + MSCs | C + M | C only | C + MSCs | C + M |
| Proximal Union | 1.5 | 0.8 | 0.2 | 1.2 | 1.3 | 1.0 |
| Distal Union | 0.5 | 1.4 | 0.7 | 1.2 | 2.0 | 1.6 |
| Core Density | 0.7 | 2.0 | 0.3 | 0.6 | 3.7 | 0.7 |
| Total Score | 2.7 | 4.2 | 1.2 | 3.0 | 7.0* | 3.3 |

Table 1. Average of radiographic scores for each implant group at each time point. C = carrier, M = marrow. Radiographs were evaluated and scored by two independent observers blinded to the identity of each implant. Union was scored both proximally and distally on a scale of 0–2. Core density was scored on a scale of 0–4. n = 3 for each group at each time point. The maximum possible total score is 8. One- way analysis of variance at the two different time points, with cell loading (none, MSCs, and marrow) as the independent variable showed significant difference between groups at 8 weeks (F = 10.9, p = 0.01) but were not significantly different at four weeks. * = significantly greater (p < 0.05) than other groups at the corresponding time point (according to post hoc Student-Newman-Keuls tests).

In the case of the defects filled with the HA/TCP carrier alone, the low scores indicate the absence of any radiodense material within the pores, and minimal union of the implant with the host bone. Loading the HA/TCP implant with fresh marrow did not result in an improvement in the healing of the defect, and the low scores reflect the similarity of this group to that of the carrier alone. However, loading the HA/TCP carrier with MSCs produces a vigorous osteogenic response. Even at four weeks, pore filling was observed and is reflected in the considerably higher scores of these implants. Interestingly, even in this case the host-implant union was modest compared to controls. By the eight week time point, the pores of the implant were filled with new bone and the host-implant union was well established.

Histologic and Histomorphometric Evaluation

Figure 4A:
FIGS. 4A–4F. Light micrographs showing representative healing of the segmental defect at four and eight weeks with various implant types. Intact limbs were harvested, fixed, dehydrated, cleared, embedded in polymethylmethacrylate, cut, and ground to 100 micron thickness prior to staining. Some animals received India ink injections to allow visualization of the vascular tree, present here in panels B, C, D, and E as black staining. The HA/TCP material artifactually appears black in these photomicrographs as a result of undecalcified processing. The cut edges of the host cortices are noted by arrowheads in a and b, and similar sections are presented in all other panels.
Figure 4B:
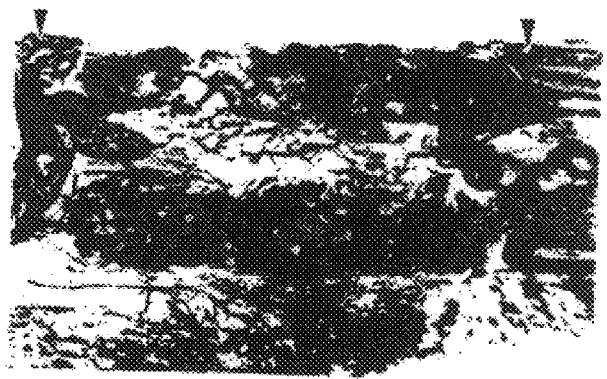

Histologic evaluation of the samples confirmed the observations made by radiography. In the empty defects, reactive bone formation appeared to emanate from the cut ends of the host cortices and endosteum. Even at eight weeks there was no bridging across the defect, and a fibrous non-union had formed at the center of the segmental gap. Photomicrographs of representative sections of the implant groups recovered at four and eight weeks are shown in FIG. 4. In defects fitted with the HA/TCP carrier alone, the pores of the implant were filled with fibrous tissue (FIG. 4A) and were well vascularized as determined by India Ink injection. No bone could be seen within the pores of the implant and there was limited integration with the host. Even at eight weeks, most of the pores were devoid of any bone despite significant vascularization evident in this photomicrograph (FIG. 4B). A small amount of new bone was present at the host-implant interfaces, and at one end of this representative implant, host-derived endosteal bone appears to be advancing into the medullary canal of the implant. Bone formation in samples loaded with fresh marrow was very similar to that of the HA/TCP carrier alone (FIGS. 4E and F). However, a modest amount of new bone could be seen within the pores of the implant at eight weeks, correlating with the results of the ectopic implants. Union of these implants was similar to that observed with cell-free implants; reactive bone formation slightly penetrated the pores at the ends of the implant.

Figure 4C:
Figure 4D:
Figure 4E:
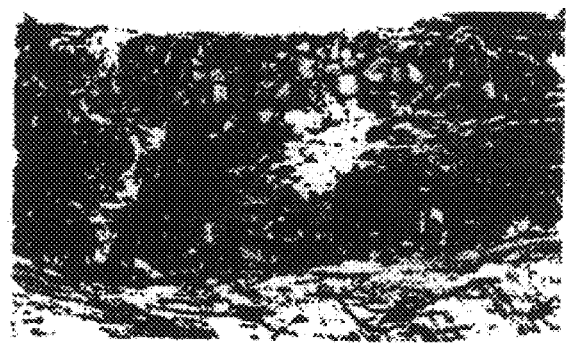
Figure 4F:
Figure 5A:
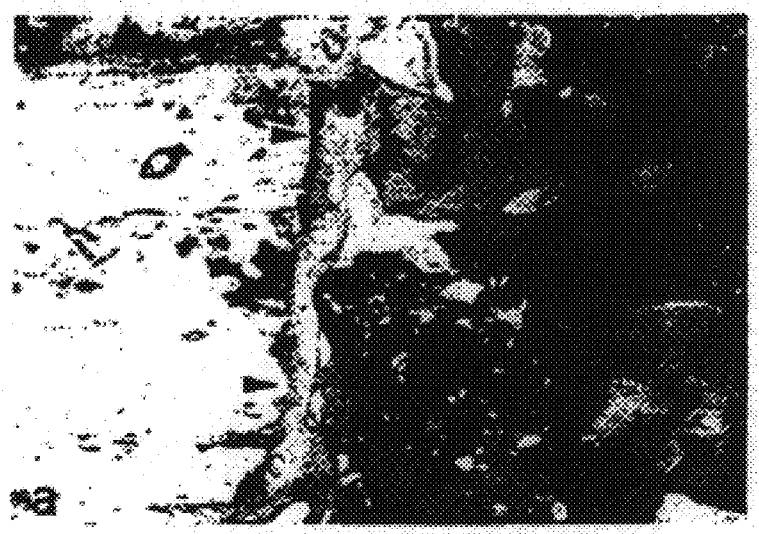
FIGS. 5A–5B. High power light micrographs showing bone regeneration at eight weeks in segmental gaps fitted with a MSC-loaded HA/TCP implant. Panel a shows the cut edge (arrowheads) of the host cortex with new bone in direct apposition. New bone at this host-implant interface is contiguous with bone formed in the pores of the HA/TCP carrier. Panel b shows both lamellar and woven bone (blue) filling the pores of the HA/TCP carrier. The carrier appears black in these images as an artifactual result of undecalcified specimen preparation. Blood vessels (v) which orient the secretory activity of osteoblasts are evident within the pores (Toluidine blue-O, x75).
Figure 5B:

In contrast to the sparse osteogenesis resulting from the addition of fresh marrow to the HA/TCP, most of the pores of the implants loaded with MSCs contained considerable new bone by four weeks (FIG. 4C). Again, there was still a clear demarcation between the cut edges of the host bone and the ends of the implant. At eight weeks nearly every pore was filled with new bone, except in some discrete areas where loading of the MSCs may have been suboptimal. Interestingly, substantial new bone formation occurred at the interface between the host and the implant, leading to a continuous span of bone across the defect (FIG. 4D). Furthermore, a periosteal callus was also present in samples loaded with MSCs (FIG. 4D), but not in other implant types. The bone formed within the pores and at the ends of these implants represents de novo bone formation, is highly cellular, and is presented in higher magnification photomicrographs in FIG. 5. New woven and lamellar bone can be seen in intimate contact with the cut edge of the host cortex at eight weeks (FIG. 5A). Importantly, this region of union is directly contiguous with bone formed throughout the pores of implant. In regions deeper within the HA/TCP, filling of the pores with new bone is evident, as is the association of vasculature which orients the secretory activity of the differentiating osteoblasts (FIG. 5B).

The results qualitatively described above are mirrored in the histomorphometric data presented in Table 2.

TABLE 2

| Carrier alone | Carrier + MSCs | Carrier + Marrow |
|---|---|---|
| 2.3 ± 1.5 | 19.3 ± 3.7* | 2.9 ± 1.7 |
| 10.4 ± 2.4 | 43.3 ± 7.7* | 17.2 ± 6.0 |

Table 2. Bone fill in HA/TCP implants as a percentage of available space. Histomorphometric measurements were obtained on the bone formed within the confines of the segmental resection, excluding the implant material itself and the medullary canal. The values are reported as means of three samples along with standard deviations from the mean. One-way analysis of variance at the two different time points, with cell loading (none, MSCs, and marrow) as the independent variable showed significant difference between MSC-loaded samples at both 4 weeks ($F = 43.3$, $p < 0.001$) and 8 weeks ($F = 26.2$, $p < 0.002$). * = significantly greater ($p < 0.01$) than other groups at the corresponding time points (according to post hoc Student-Newman-Keuls tests). No difference was observed between marrow and carrier alone at either time point ($p > 0.1$).

The cell-free HA/TCP implants had a bone fraction of only 2.3% and 10.4% at four and eight weeks, respectively. Importantly, this fraction of bone at eight weeks correlates with previously published results (126). These fractions primarily represent the bone ingrowth from the cut ends of the host cortices. The marrow-loaded HA/TCP cylinders did exhibit modest osteogenesis within the body of the implant and consequently had a slightly higher value of 17.2% at eight weeks. Importantly, by four weeks, the MSC-loaded samples exceeded the eight week value for the other two groups. The 19.3% bone fill at this four week time point is most likely attributable to MSC-mediated osteogenesis. The average bone fraction within the implant increased over time, reaching 43% by eight weeks. One-way ANOVA performed on the data along with the Student-Newman-Keuls tests showed that at both four and eight weeks, the MSC treatment was significantly better than the carrier alone or the marrow-loaded carrier ($p<0.01$). No significant difference between carrier alone and marrow-loaded implants was detected. The volume fraction of the HA/TCP carrier remained constant, and served as an internal control for the histomorphometry system. Even though the empty defects had 34% bone fill by eight weeks, there was no bridging across the defect, and thus would be classified as a clinical non-union.

Discussion

In the present study, we have demonstrated that purified, culture-expanded syngeneic progenitor cells are capable of healing a clinically significant bone defect in a well established animal model. These progenitor cells are referred to as mesenchymal stem cells since they give rise not only to bone (1,19,23), but to cartilage (24,35,53), muscle (48,54), tendon (6), and a stromal tissue which supports hematopoietic differentiation (38). While the osteogenic potential of both animal and human MSCs has been proven via subcutaneous implants in ectopic assays, rigorous and quantitative studies establishing the ability of culture-expanded MSCs to regenerate large segmental bone defects have not been reported to our knowledge. The combination of MSCs with a porous HA/TCP implant material are shown in the present study to be an effective strategy for healing large segmental bone defects. The current investigation further substantiates that compared to fresh marrow, MSCs produce significantly more bone when placed in either an ectopic or an orthotopic site. With these results as a foundation, we may begin to refine our approach to cell therapies for the regeneration of skeletal defects.

To further characterize the cells used in this study, we cultured them in the presence and absence of a medium which induces osteogenic differentiation in vitro. As has been reported in numerous other laboratories (32,39,47,52), these rat marrow-derived cells develop along the osteogenic lineage in response to dexamethasone, eventually forming mineralized nodules of bone-like tissue on the surface of the dish. Such differentiation is evident in our photomicrographs (FIG. 1), and serves to document that the cells used in these implants indeed possess the ability to form bone, one of the inherent properties of MSCs. Furthermore, the bone and cartilage formed in cubes implanted subcutaneously not only confirms the osteochondral potential of the MSCs, but acts as an internal control to verify that every host rat was capable of providing an environment which could support osteogenesis within these combined cell:matrix implants. Additional experiments documenting the multilineage potential of these cells were not included as part of the current study because previous publications have focused on describing such potential in greater detail (34,35,48,54). The isolation and selection procedures for rat MSCs are similar to those used for human MSCs (19,35), and result in the formation of characteristic primary colonies illustrated in FIG. 1A. These cells are mitotically expanded to yield a morphologically homogeneous population which divides uniformly across the dish. Both human and rat MSCs have been shown to possess multilineage potential, and the details of in vitro osteogenic differentiation of human MSCs has recently been reported (10,23). Conditions for the isolation and culture expansion of human MSCs without lineage progression have been optimized (3,19,35), and the development of a serum free medium for human MSC growth has been completed (58).

The radiographic findings in this study establish a precedent for obtaining non-invasive evidence of bone regeneration in animals, or humans, which receive MSCs in an orthotopic location. Given the porous nature of the HA/TCP implants, new bone which forms within the interstices of the material is readily apparent radiographically by four weeks, in spite of the inherent radiodensity of the HA/TCP material. The progressive increase in radiodensity evident by eight weeks correlates well with the histological observations of processed limbs. Interestingly, despite the presence of new bone within the core of implants by four weeks, integration at the host-implant interface was not observed until eight weeks. The mean radiographic scores for the three implant groups document a significant ($p<0.05$) difference between MSCs and either marrow-loaded and ceramic implants at eight weeks, while no significant difference was observed between marrow-loaded and ceramic implants at either time point.

The histologic studies demonstrate appositional bone growth on the surface of the HA/TCP throughout the core of the implant, consistent with previous observations of osteogenesis in ectopic implants loaded with MSCs (19). The bone which is formed at four and eight weeks in MSC-loaded samples is woven in many areas, but lamellar bone can also be appreciated (FIGS. 5A and 5B). It is critical to note that in the process of regenerating this osseous defect, bone formation occurs by a direct conversion of mesenchymal cells into osteoblasts rather than by an endochondral sequence. As regeneration of the bone at the defect site continues, the pores of the ceramic are filled with significantly more bone, which is laid down upon the walls of the implant or existing bone, and oriented by the invading vasculature. These blood vessels, visualized by India inking of animals immediately prior to sacrifice, also provide a portal for the entry and establishment of new marrow islands which contain hematopoietic elements, as well as host-derived MSCs. The process of bone remodeling ensues, and eventually the donor bone is replaced by host bone. At the edge of the defect, integration of the implant is achieved with direct continuity between the cut edge of the host cortex and the new bone formed upon the surface of the implant (FIG. 5A). Since only minimal host-implant union occurs in rats provided with either marrow-loaded or cell-free ceramics, the advanced integration observed in MSC-loaded ceramics likely reflects the combined contributions of implanted MSCs and host-derived cells. The lack of early union in all samples was surprising in light of the fact that defects which were left empty underwent a substantial amount of reactive bone formation at the cut edges of the cortices. It is possible that the presence of an implant in the defect site inhibits migration and/or prolapse of the surrounding loose mesenchyme which contributes to the reactive bone formation in the empty defects. Furthermore, micromotion of the implanted cylinders would likely hinder stable union at the interface.

The ability of MSCs to regenerate a large segmental defect in this experimental model compares favorably with other investigations testing implants such as demineralized bone matrix, bone marrow, purified or recombinant BMPs, allograft, ceramics, and fibermetals (12,29,37,50,55,56). While the use of recombinant BMP has received considerable attention, the precise mechanism of action has only recently been appreciated. These powerful inductive molecules act on undifferentiated mesenchymal cells to initiate the endochondral cascade, ultimately resulting in the formation of bone. Studies of undifferentiated rat marrow stromal cells confirm that BMP-2 acts to directly stimulate osteoblast development, and that this stimulation is enhanced by the addition of dexamethasone (32). Others have shown that bone formation occurs in an orthotopic site when fresh marrow alone is added, but the rate and extent of healing is a function of the amount of marrow and the number of osteoprogenitor cells residing therein (15,55). An important set of experiments by Takagi and Urist demonstrate that the addition of BMP is not effective at healing segmental defects when access to the medullary canal and the marrow stroma is prevented, thus indicating an absolute requirement for the cellular constituents of marrow in BMP-mediated bone repair. These results were bolstered by studies indicating that the implantation of fresh marrow along with BMP in a rat segmental gap model is more effective than either component implanted alone (29). One may conclude from all of the above that marrow-derived mesenchymal progenitors, or MSCs, are the target for endogenous osteoinductive molecules, such as BMPs, which are released during normal bone healing. It therefore follows that one must have an adequate supply of MSCs in order to respond to the normal (or exogenously supplied) signals of bone repair, or healing will be effete.

The histomorphometric data generated in this study provides a basis for comparison to other investigations. When fresh marrow from one femur equivalent is loaded on an HA/TCP implant, no significant difference in bone formation is observed when compared to implants which receive no cells. This is true for both time points in our study, and likely reflects an inadequate number of MSCs in the volume of marrow applied. Had we loaded the implants with considerably more marrow, we and others would predict that greater healing of the bone defect would have occurred (29,55). Nevertheless, an appropriate clinically relevant control is generously approximated by applying the total cell population obtained from one long bone since removing all the marrow from multiple long bones for the repair of a focal defect is contradictory to sound clinical judgment. Perhaps most importantly, MSCs produced a bone fill of 19.3% and 43.2%, respectively, at four and eight weeks. When purified BMP was applied to an identical carrier in the same experimental model, the bone fill was 21% at four weeks, and only 22% by eight weeks (50). These BMP-coated HA/TCP implants did not achieve a bone fill of 43 percent until 16 weeks following implantation. While similar amounts of bone resulted from both implant types at four weeks, MSCs produce twice as much bone as BMP by the eight week time point. In this formulation, it took BMP sixteen weeks to form the same amount of bone which MSCs produce in only eight weeks. On this basis, it appears that MSCs offer a considerable advantage to the use of BMP alone, although some combination of BMP and MSCs could provide an even faster, more vigorous bone repair as discussed above.

Since the number of progenitor cells present at the site of repair is a critical factor, it is obligatory to estimate how the MSC-loaded implants compare with marrow-loaded implants in this regard. The number of nucleated marrow cells which were placed on an implant was approximately fifty million; the same number harvested from one long bone. Another fifty million cells were used to initiate the MSC culture which eventually provided cells for one implant. From these fifty million cells, roughly 500 MSC colonies develop, and these cells are mitotically expanded to three million by the end of first passage. This represents a 6,000-fold increase in MSC number due to approximately twelve population doublings. Using the current technique to load these type of implants, it appears that only about 150,000 cells become adherent following incubation with the MSC suspension. Nevertheless, the local administration of 150,000 purified MSCs would increase the number of progenitor cells 300 times over the number normally present in fifty million unfractionated marrow cells. On the basis of these calculations, the advantage which this technique offers over other bone regeneration strategies is direct delivery of the cellular machinery required for bone formation. This approach would have an extraordinary advantage in settings where the number of endogenous progenitor cells is reduced, such as that which occurs in ageing, osteoporosis, or a variety of other pathologic conditions (10,28,36,47,51, 52). Other investigators have pursued this logic by attempting to deliver more progenitor cells simply by concentrating the marrow, by crude fractionation and removal of red blood cells, or by cultivating the stromal cells in vitro (37,41,55).

Now that techniques and conditions have been established which support the expansion of purified human MSCs in culture as much as one billion fold without a loss in osteogenic potential (3), analogous clinical protocols for regenerating human bone defects are not far away. It will be possible to further expedite the healing process by directing these culture-expanded MSCs ex vivo to enter the osteogenic lineage prior to implantation, thus decreasing the in situ interval between implantation and their biosynthetic activity as osteoblasts. Additional efforts are underway to develop cell delivery vehicles which will provide more flexibility to the surgeon, including materials which can be shaped to fit any type of defect. By combining a pharmacologic stimulus, such as BMP, with an even better delivery vehicle, we will be able to offer patients therapeutic options which have never before been available.

EXAMPLE 2

Large Segmental Canine Femoral Defects are Healed with Autologous Mesenchymal Stem Cell Therapy This study demonstrates that culture-expanded, autologous mesenchymal stem cells can regenerate clinically significant bone defects in a large animal model.

Recently, the ability of syngeneic bone marrow-derived mesenchymal stem cells (MSCs) to repair large segmental defects in rodents was established (25). These MSCs may be isolated from marrow or periosteum, expanded in number ex vivo, and delivered back to the host in an appropriate carrier vehicle. Studies in rats demonstrated that the amount of bone formed 8 weeks following implantation of MSCs was twice that resulting from BMP delivered in the same carrier (25,50). In order to demonstrate clinical feasibility of this technology, our objective was to regenerate segmental bone defects in a large animal amenable to stringent biomechanical testing. To achieve this goal, we developed a canine femoral gap model to compare radiographic, histologic, and biomechanical data following implantation of an MSC-loaded carrier, carrier alone, and cancellous autograft bone.

Materials and Methods
MSC Cultivation and Manipulation

A 15 cc bone marrow aspirate was obtained from the iliac crest of each animal, according to an IACUC-approved protocol, and shipped on ice by overnight courier to the cell culture facilities. Isolation of canine MSCs was achieved by centrifuging whole marrow aspirates over a Percoll cushion, using procedures analogous to those developed for human MSC isolation (19). Tissue culture flasks (185 $cm^2$) were seeded with $10^7$ nucleated cells isolated from the cushion, and cultured with DMEM containing 10% fetal calf serum from a selected lot (35). Cells were passaged at $8 \times 10^3$ cells/$cm^2$, and transported back to the veterinary hospital where they were maintained until the time of implantation. Cell-loaded implants were prepared by incubating fibronectin-coated porous hydroxyapatite-tricalcium phosphate (HA/TCP) cylinders (Zimmer, Inc.) in a $7.5 \times 10^6$ cells/ml suspension of MSCs for 3 hr at 37° C. The interval between marrow harvest and implantation was 16 days. An aliquot of cells from each preparation was also cultured under osteoinductive conditions to quantify aspects of osteoblastic differentiation.

Canine Femoral Gap Model

A unilateral segmental femoral defect model was developed for this study following IACUC approval. Under general anesthesia, thirty-six skeletally mature female purpose-bred hounds (20 kg) underwent resection of a 21 mm long osteoperiosteal segment from their mid-diaphysis. A 4.5 mm Synthes® 8-hole lengthening plate was contoured to the lateral aspect of the bone, and secured with bicortical screws. The defect was filled with one of three materials; 1) a cell-free HA/TCP cylinder, 2) an MSC-loaded HA/TCP cylinder, or 3) cancellous bone harvested from the iliac crest. HA/TCP implants were secured by placing two sutures around the implant and the plate. Animals received peri-operative antibiotics, and analgesics were administered for three days post-operatively.

Radiographic and Histologic Analyses

Standard radiographic images were obtained at pre-op, immediately post-op, and at 4 week intervals until termination of the study. All samples contained a radiodensity step wedge to provide a basis for comparing changes over time, and between dogs. Upon sacrifice, specimens were subjected to high resolution Faxitron radiography, and subsequently processed for biomechanical evaluation. Following torsion testing, undecalcified longitudinal sections will be processed for quantitative histomorphometry.

Biomechanical Testing

Sixteen weeks after implantation, animals were sacrificed for torsion testing of femurs. The fixation plate, screws, and adherent soft tissue were removed, and the metaphyses of the bones were embedded. The specimens were externally rotated in a custom torsion test apparatus, failure load and stiffness recorded, and the data analyzed by one way ANOVA according to post hoc Student-Newman-Keuls tests.

Results

All animals tolerated the surgical procedure well, with no incidence of infection, implant rejection, or failure of fixation. Two modes of repair were apparent in the MSC-loaded samples; first, considerable callus formation occurred at both host-implant interfaces; and second, a substantial collar of bone surrounding the implant itself developed. Cell-free implants did not possess either of these features. Autograft samples underwent a traditional consolidation sequence, with the majority of bone laid down in the medial aspect of the gap defect. MSC-loaded samples not only became fully integrated at the host implant interface, but the periosteal collar extended proximally and distally beyond the cut edges of the gap. Furthermore, the diameter of new bone at the mid-diaphysis was greater in MSC-loaded implants than either autograft samples or intact limbs. in vitro analyses of the osteogenic potential MSCs from each animal demonstrate the development of alkaline phosphatase-positive cells which deposit significant mineralized extracellular matrix.

TABLE 3

Histomorphometric and Histologic Features of Bone Regeneration Sixteen Weeks Following Implantation of Ceramic Cylinders (C) or Ceramic Cylinders plus Autologous Mesenchymal Stem Cells (M)

| Dog # | Ceramic Area (%) | Bone Area (%) | Soft Tissue Area (%) | Average Thickness of Peri-implant Callus (Medial Surface) (mm) | Interface Union |
|---|---|---|---|---|---|
| C1 | 34.0 | 7.6 | 92.4 | 0.00 | 1 |
| C2 | 33.6 | 35.4 | 64.6 | 0.00 | 4 |
| C3 | 45.3 | 7.3 | 92.6 | 0.00 | — |
| C4 | 33.7 | 23.5 | 76.5 | 0.00 | 4 |
| C5 | 35.9 | 47.0 | 53.0 | 0.00 | 4 |
| C6 | 28.1 | 23.1 | 76.9 | 0.00 | 4 |
| Mean | 35.1 | 24.0 | 76.0 | 0.00 | 3.4 |
| M1 | 40.2 | 41.9 | 58.1 | 0.33 | 4 |
| M2 | 38.2 | 38.5 | 61.5 | 3.17 | 4 |

TABLE 3-continued

Histomorphometric and Histologic Features of
Bone Regeneration Sixteen Weeks
Following Implantation of Ceramic Cylinders (C)
or Ceramic Cylinders plus Autologous Mesenchymal Stem Cells (M)

| Dog # | Ceramic Area (%) | Bone Area (%) | Soft Tissue Area (%) | Average Thickness of Peri-implant Callus (Medial Surface) (mm) | Interface Union |
|---|---|---|---|---|---|
| M3 | 33.8 | 42.6 | 57.4 | 2.50 | 4 |
| M4 | 39.2 | 37.0 | 63.0 | 0.67 | 4 |
| M5 | 28.0 | 30.5 | 69.5 | 2.00 | 4 |
| M6 | 32.6 | 48.7 | 51.3 | 0.67 | 4 |
| Mean | 35.3 | 39.9* | 60.1* | 1.56* | 4.0 |

*$P < 0.05$ compared to Control implants.

In the case of the MSC-loaded samples, in addition to the considerable amount of bone in the confines of the ceramic block, there was also a fairly large mineralized periosteal callus. Also, the marrow space was reestablished within the defect. Whereas in the cell-free HA/TCP cylinders, most of the bone present was in the endosteal space with some penetration into the implant.

Torsional testing of the samples (n=6 per group) showed that the MSC-loaded samples were almost twice as long as the cell free examples, but were only a third as strong as autograft controls.

Discussion

The present study demonstrates that MSCs from a large animal may be culture-expanded, and implanted for the successful repair of large diaphyseal bone defects. Radiographic and histologic evidence indicates that not only do the MSCs form bone within and around the implant directly, but their presence elicits a response in the host periosteum to form additional bone. The mechanism of this is currently not known, but is consistent with our observation that MSCs undergoing osteogenic differentiation secrete a paracrine factor(s) which is osteoinductive (22). The conspicuous lack of callus formation and periosteal reaction in the cell-free implants was an unexpected finding. In addition to establishing a new standardized model for large animal bone repair, this study illustrates the feasibility of translating autologous stem cell therapy from the laboratory into the clinic.

EXAMPLE 3 in vivo Bone Formation Using Human Mesenchymal Stem Cells

Although rat MSCs have been shown to synthesize structurally competent bone in an orthotopic site (25), human MSCs have only been shown to form bone in vitro (2,23) and in an ectopic implantation site in immunodeficient mice. Since fracture healing and bone repair depend on the ability to amass enough cells at the defect site to form a repair blastema, one therapeutic strategy is to directly administer the precursor cells to the site in need of repair. This approach is particularly attractive for patients who have fractures which are difficult to heal, or patients who have a decline in their MSC repository as a result of age (28,47), osteoporosis (51), or other metabolic derangement. With this in mind, the goal of the current study was to show that purified, culture-expanded human MSCs are capable of regenerating bone at the site of a clinically significant defect.

Materials and Methods

Human MSC Cultivation and Manipulation

Isolation and culture-expansion of human MSCs from a bone marrow aspirate obtained from a normal volunteer after informed consent was conducted as previously described (17,19). Following initial plating in Dulbecco's Modified Eagle's Medium (Sigma) containing 10% fetal bovine serum (BioCell) from a selected lot (35), non-adherent cells were removed on day 3 at the time of the first medium change, and fresh medium was replaced twice weekly thereafter. Adherent MSCs represent approximately 1 in $10^5$ nucleated cells originally plated. When culture dishes became near-confluent, cells were detached and serially subcultured.

In Vitro Osteogenic Assays

Human MSCs were replated into six-well dishes at a density of $3 \times 10^3$ cells/cm². The following day (Day 0), fresh medium was provided, and the cells were grown in the absence or presence of Osteogenic Supplements (OS) (2,23). Media changes were performed twice weekly, and at days 4, 8, 12 and 16, cultures were assayed for cell number, alkaline phosphatase (APase) biochemistry and histochemistry, and mineralized matrix production utilizing techniques previously described (23).

Implant Preparation

Porous hydroxyapatite/β-tricalcium phosphate (HA/TCP) ceramic blocks, mean pore size 200–450 μm (Zimmer, Inc., Warsaw, Ind.), were shaped into cylinders approximately 4 mm in diameter and 8 mm in length with a 1 mm central canal, or cut into cubes 3 mm per side. MSC-loaded implants were prepared by incubating human fibronectin-coated HA/TCP cubes and cylinders in a $7.5 \times 10^6$ cell/ml suspension of first passage MSCs for 2 hr at 37° C. as previously described (25). Cell-free control cylinders were prepared identically.

Athymic Rat Femoral Gap Model

The femoral gap surgical model employed here has been used extensively in euthymic rats to study long bone repair (25). Briefly, both femurs of Harlan Nude (Hsd:Rh-rnu) rats (325 g) were exposed by an anterolateral approach. A polyethylene fixation plate was attached to each femur by four Kirschner wires, and an 8 mm transverse segment of the central diaphysis, along with its adherent periosteum, was removed by using a rotary osteotomy burr under saline irrigation. Each animal then received a cell-free HA/TCP cylinder in one femoral defect, an identical cylinder loaded with human MSCs in the contralateral defect, and a subcutaneous implant of a MSC-loaded HA/TCP cube along the dorsum.

Radiography

Immediately after sacrifice at each time point, all specimens were radiographed in a lateral position using a high resolution Faxitron Imaging system with an exposure of 35 kVP for 30 sec.

Quantitative Histomorphometry and Immunochemistry

Upon sacrifice at 4, 8, and 12 weeks, a minimum of 3 specimens of each type were processed for undecalcified histology following radiography. Longitudinal sections were cut, stained with Toluidine blue-O, and quantitative assessment of bone formation was performed using Leica Quantimet 500MC image analysis software as previously described (25). The data were analyzed by Student's t-test. Subcutaneously implanted samples were fixed in formalin, decalcified, embedded in paraffin, serially sectioned, and similarly stained. Limbs from one animal at each time point were also prepared for immunostaining by monoclonal antibody 6E2, which distinguishes human cells from rat cells (19). Undecalcified cryosections were incubated with 6E2 supernatant, or an irrelevant primary monoclonal antibody control (SB-1), followed by FITC-conjugated goat anti-mouse IgG secondary antibody (GIBCO) diluted 1:500 in phosphate-buffered saline.

Biomechanical Testing

Twelve weeks after implantation, 7 experimental animals and 6 unoperated control animals were sacrificed for torsion testing of femurs as previously described (81). The fixation plate and adherent soft tissue were removed, and the metaphyses of the bones were embedded. The specimens were externally rotated in a custom torsion test apparatus, failure load and stiffness recorded, and the data analyzed by one way ANOVA with post hoc Student-Newman-Keuls tests.

Results

MSC Cultivation and Osteogenic Differentiation in vitro

Figure 6A:
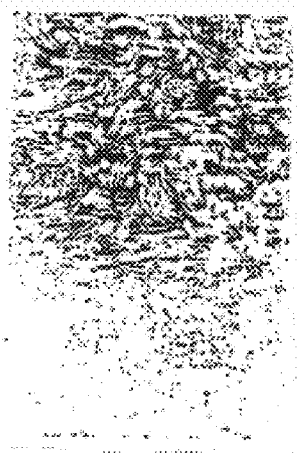
FIG. 6A. First-passage MSCs display characteristic spindle-shaped morphology and are distributed evenly across the surface of the dish after replating.

Human MSC cultures were established and, by 7 days, formed characteristic colonies on the surface of the culture dish. Primary colonies which were subcultivated on day 14 attached uniformly to the surface of new dishes, and were allowed to divide for another 7 days until they became ~85% confluent. Passaged cells demonstrated their characteristic spindle-shaped morphology (FIG. 6A), and uniformly divided resulting in an even distribution of MSCs throughout the plate. Cells derived from this first passage were used for preparing implants as previously described, and an aliquot was used to confirm their osteogenic potential in vitro.

Figure 6B:
FIG. 6B. MSC cultures grown in the presence of OS for 16 days form mineralized nodular aggregates which stain gray for APase and black for mineralized matrix (Unstained (a) x18, APase and von Kossa histochemistry (b), x45).
Figure 6C:
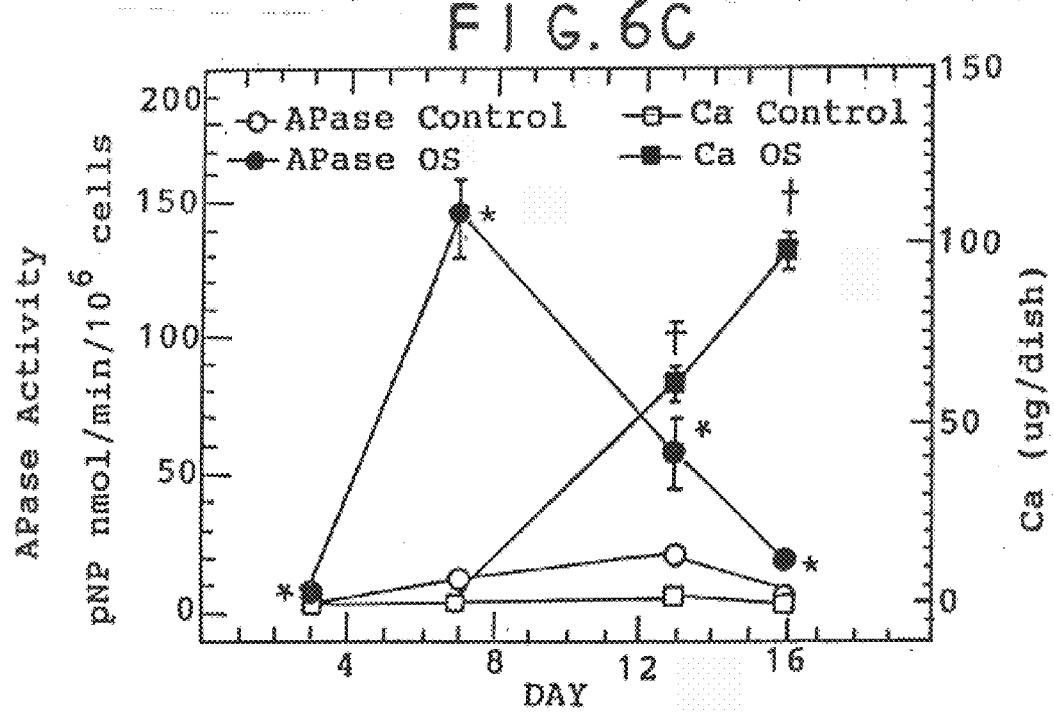
FIG. 6C. APase activity and calcium deposition in MSC cultures grown in Control or OS Medium on days 4, 8, 12 and 16. Samples were harvested at the indicated days, and APase activity, cell number, and calcium deposition were determined as described in Materials and Methods. The results represent the mean±SD of triplicate cultures from first passage cells. *$P<0.05$, †$<0.005$ (compared to Control).

As described in previous studies (2,3,23), MSCs cultured with OS underwent a dramatic change in cellular morphology from that of spindle-shaped to cuboidal, which was accompanied by an increase in APase activity and production of an extracellular matrix rich in bone hydroxyapatite (FIG. 6B). A significant increase in APase activity was observed after 4 days of OS treatment with maximal activity occurring on day 8, followed by a decline through day 16 (FIG. 6C). This late decrease in APase activity of OS cultures correlates with increasing mineral deposition and terminal differentiation of cells into osteocytes. While no calcium deposition was detected either by Von Kossa staining or the sensitive colorimetric quantitative calcium assay in Control cultures, FIG. 6C illustrates that MSCs grown with OS deposited a significant amount of calcium by days 12 (60±5.1 $\mu$g/dish) and 16 (98±5.0 $\mu$g/dish).

MSC-Mediated Osteogenesis in Ectopic HA/TCP Implants

Figure 7:
FIG. 7. Light micrograph of a representative histological section from a human MSC-loaded HA/TCP implant placed ectopically in subcutaneous tissue of an athymic rat. MSCs were loaded into the ceramic, implanted as described in Materials and Methods, harvested at 12 weeks, decalcified and processed in paraffin for microscopy. Only remnants of the HA/TCP ceramic (c) remain, while the pores of the implant are filled with bone (b), blood vessels (arrow) or fibrous tissue (f). Cuboidal osteoblasts are seen lining the surface of the developing bone. (Toluidine blue-O, x75).

Human MSC-loaded HA/TCP cubes implanted in the subcutaneous space of athymic rats displayed evidence of osteogenesis by 4 weeks, but considerably more bone was present within the pores at 8 and 12 weeks. A representative section from a MSC-loaded cube harvested 12 weeks following implantation is shown in FIG. 7. Bone formation occurs within the pores of the cubes, and is associated with vascular elements which penetrate the implant. Such angiogenesis is obligatory to new bone formation since the secretory activity of osteoblasts is an oriented phenomenon guided by vasculature (8). As previously demonstrated (19), cubes implanted without MSCs never contained bone but were filled with fibrous tissue and blood vessels only.

Osteotomy Model and Radiography

Figure 8A:
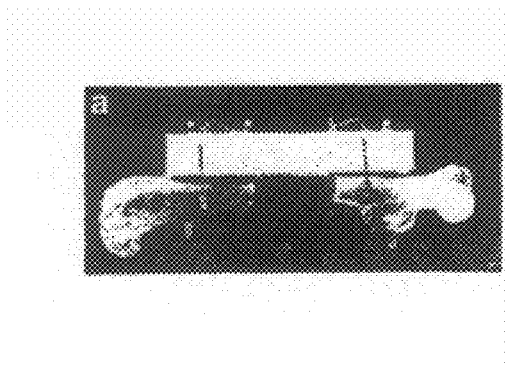
FIG. 8. Segmental gap defect model and radiography. (a) A polyethylene fixation plate is positioned on the lateral aspect of this representative rat femur. Four bicortical screws and 2 cerclage wires are used to secure the plate in place. An 8 mm segment of bone is removed along with its adherent periosteum, and a ceramic implant, with or without cells, is placed into the defect site. The overlying muscles are returned to their proper anatomic position, and the skin is closed with resorbable sutures. High resolution radiographs obtained immediately following sacrifice show the extent of healing of the segmental defect at 12 weeks with the 2 implant types (b, c). While total integration of the implant at the host-ceramic interface is evident in the carrier plus MSC group (b), only modest union is observed in the cell-free implants (c). The pores of the MSC-loaded implant are filled with bone throughout the gap, but the cell-free carrier contains little bone and several cracks.
Figure 8B:
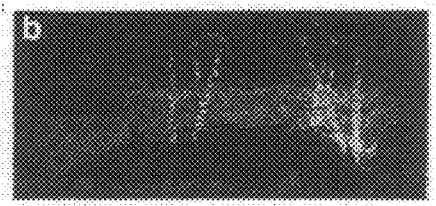
Figure 8C:
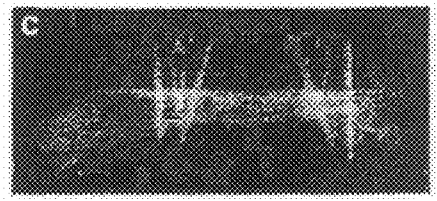

FIG. 8A illustrates the segmental defect model used in this study. The polyethylene fixation plate on top of the femur provides stability following creation of the 8 mm diaphyseal defect. No animals experienced failure of fixation or other post-operative complications throughout the course of study. Previous studies have established that femoral defects that are not implanted with a bioactive material give rise to a fibrous non-union devoid of bone (25). High resolution Faxitron radiographs provided sufficient clarity and detail to discern subtle changes occurring within the implant and the surrounding host bone. Representative radiographs of the femurs from the 2 groups recovered 12 weeks post-implantation demonstrate substantially more bone in animals which received MSC-loaded HA/TCP cylinders (FIG. 8B) versus cell-free cylinders (FIG. 8C). Increasing radiodensity, and obliteration of the apparent pore structure, was used as an indication of new bone formation within the core of the implant. Although integration of the implant, or union, was not generally observed by 4 weeks, the subsequent formation of a radiodense bone bridge between the implant and the host at 8 weeks completely masked the interface. By 8 weeks, the MSC-loaded implant contained considerable bone within the pores and was integrated with the host bone at the ends of the implant. At 12 weeks, union was complete and additional bone was evident in the pores. Callus formation along the fixation plate was observed in some samples, as was an occasional eccentric spicule of bone usually present along the medial aspect of the femur. Some specimens, both with and without cells, contained cracks within the core of the implant.

Immunocytochemical Evaluation

Figure 9A:
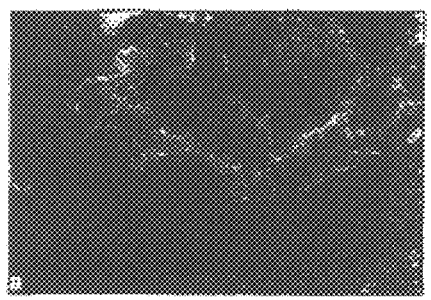
FIG. 9. Histologic representation of bone regeneration in segmental femoral defects. Immunohistochemical staining with antibody 6E2 (a) demonstrates that 4 weeks following implantation of a MSC-loaded sample, the cells within the pores of the carrier are reactive on their surface, and therefore of human origin, while cells outside the ceramic are not immunoreactive. In phase contrast microscopy (b), the ceramic is black, and cells in the pores and surrounding the outside of the implant are evident. The ceramic material itself adsorbs fluorescent secondary antibody and appears green (a, b, x75). Light micrographs showing representative healing of a segmental defect implanted with HA/TCP carrier alone (a), or carrier plus MSCs (c,e,f), 12 weeks after implantation. Limbs were harvested, fixed, dehydrated, cleared, embedded in polymethylmethacrylate, cut, and ground to a thickness of 100 µm for staining. The ceramic appears black in these photomicrographs as an artifact of undecalcified specimen preparation, and bone present within the pores or at the host-implant interface appears blue-violet. The MSC-loaded specimen shown here was subjected to destructive mechanical torsion testing, and was subsequently processed for histology in two separate pieces. Repositioning photomicrographs of the two pieces approximates the appearance of the femur prior to testing (c). The actual fracture plane is denoted by the double arrows above and below the implant. The cut edges of the host cortices are noted by arrowheads in c, d, and e. Only samples containing a MSC-loaded implant effectively heal the defect. Higher power micrographs demonstrate the substantial amount of bone present at the host-implant interface (e) and within the body of the implant (f). (Toluidine blue-O, (c, d) x7, (e) x31, (f) x45).
Figure 9B:
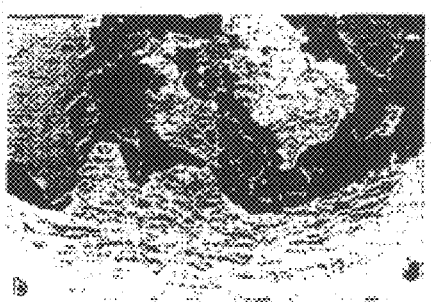

Immunocytochemical staining with antibody 6E2 demonstrates that, at 4 weeks, virtually all the cells within the pores of the implant were reactive on their surface and were, therefore, of human origin (FIG. 9A). Along the immediate periphery of the implant, the host rat cells were intermingled with the human donor cells, but as the distance away from the surface of the implant increased, the representation of donor cells precipitously declined. The presence of these peripheral cells which are not immunostained also serves as a negative control for this established antibody. The ceramic material itself, which appears black in the phase contrast micrograph (FIG. 9B), displays a high level of background fluorescence. The exquisite sensitivity of the 6E2 antigen:antibody interaction necessitated that we use unfixed frozen sections which, unfortunately, limited our ability to process these calcified tissue specimens for immunostaining. While we were able to obtain satisfactory cryosections of 4 week samples (shown here), we were unable to prepare sections from later samples which contained substantially more bone.

Histologic Evaluation

Figure 9C:
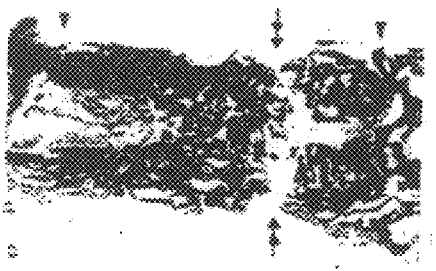

Analysis of the Toluidine blue-O-stained samples confirmed the observations made by radiography. Photomicrographs of representative sections of the implant groups recovered at 12 weeks are shown in FIG. 9. Most of the pores of the implants loaded with MSCs contained substantial new bone by 8 weeks, and this process of bone regeneration continued through the 12 week assessment period (FIG. 9C). At 8 weeks nearly all pores contained new bone, except in some discrete areas where loading of the MSCs may have been compromised. Evaluation of limbs following biomechanical testing indicates that fractures were of a transverse or spiral nature, and were generally propagated through a central region of the implant containing cartilage or a modest amount of bone, as seen in FIG. 9C. During the regenerative process, substantial new bone formation occurred at the interface between the host and the implant, leading to a continuous span of bone across the defect. New woven and lamellar bone can be seen in intimate contact with the cut edge of the host cortex at 12 weeks (FIG. 9E), and this region of union is directly contiguous with bone formed throughout the pores of implant. In regions deeper within the HA/TCP (FIG. 9F), filling of the pores with new bone and vasculature is evident.

Figure 9D:
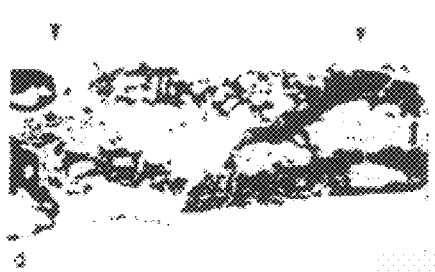
Figure 9E:
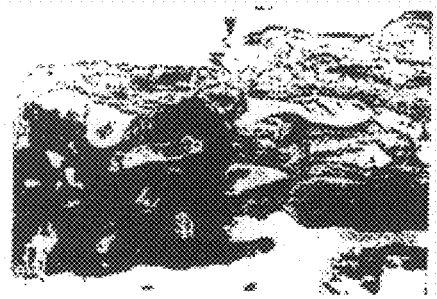
Figure 9F:

In defects fitted with the HA/TCP carrier alone, the pores of the implant were predominantly filled with fibrous tissue even at 12 weeks (FIG. 9D). Many samples had evidence of modest integration at the host-implant interfaces, and at one end of this representative implant (FIG. 9D), host-derived endosteal bone appears to be advancing into the medullary canal of the carrier as a result of osteoconduction. None of the cell-free ceramic carriers contained bone throughout the pores of the implant.

Histomorphometric Evaluation

The results qualitatively described above are mirrored in the histomorphometric data presented in Table 4.

TABLE 4

Bone Fill in HA/TCP Implants as a Percentage of Available Space

|  | Four Weeks | Eight Weeks | Twelve Weeks |
| --- | --- | --- | --- |
| Carrier Alone | 1.89 ± 1.00 | 11.47 ± 7.08 | 29.51 ± 8.93 |
| Carrier plus MSCs | 1.95 ± 1.92 | 26.46 ± 3.60* | 46.61 ± 14.83* |

Table 4. Longitudinal sections through the segmental defect of athymic rats implanted with ceramic carriers, with and without human MSCs, were evaluated histomorphometrically for bone content. The results represent the mean ± SD of 3 experimental limbs of each group at 4 and 8 weeks, and 8 limbs of each group at 12 weeks. *P < 0.05 compared to the carrier alone at each time point.

Bone present in the cell-free HA/TCP implants primarily represents the bony ingrowth from the cut ends of the host cortices. At 4 weeks and beyond, the MSC-loaded samples contained significantly more bone than the cell-free group, and the average bone fraction within the implant increased over time, reaching 26.5% and 46.6% by the 8 and 12 week time points, respectively. This increased bone fraction at 8 weeks is 2.3-fold higher than that measured in cell-free implants at the same time, and by 12 weeks, is over 23-fold higher than that observed in either condition at 4 weeks. The volume fraction of the HA/TCP carrier remained constant, and served as an internal control for histomorphometry.

Mechanical Testing

Twelve experimental and 11 intact femora from age and weight-matched control animals were tested in torsion 12 weeks after implantation. Two experimental limbs were not tested because they were extremely fragile. Gross inspection of the healed defects revealed a distal varus rotation deformation in most specimens. Table 5 summarizes the mechanical testing results in terms of torsional strength, stiffness, and total energy absorbed.

TABLE 5

Mechanical Properties of Rat Femora 12 Weeks after Implantation

|  | Intact Control | Carrier Alone | Carrier + MSCs |
| --- | --- | --- | --- |
| Strength(N mm) | 409 ± 71 | 74 ± 63 | 159 ± 37 |
| Stiffness(N mm/deg) | 39 ± 5.5 | 6.6 ± 4.2 | 16.2 ± 4.0 |
| Energy(N mm × deg) | 2.6 ± 0.7 | 0.6 ± 0.4 | 1.3 ± 0.8 |

Table 5. Mechanical testing data on rat femur samples from unoperated age matched controls (Intact Control), or animals whose segmental defects were implanted with the HA/TCP carrier alone (Carrier alone) or the MSC-loaded HA/TCP (Carrier + MSCs). These results represent the mean ± SD of 6 limbs from each experimental implant group, and 11 limbs from control animals. Twelve weeks after implantation, each specimen was harvested, the ends of the bone were embedded, and the samples were tested in external rotation at 6 degrees/second along the longitudinal axis until failure. One-way ANOVA on each of the parameters showed a significant difference between the groups at P < 0.0001. Furthermore, each of the groups were significantly different from the other for strength and stiffness (P < 0.05), as determined by post hoc Student-Newman-Keuls tests.

These results demonstrate a 115%, 145% and 112% increase in strength, stiffness and torsional energy absorbed, respectively, in MSC-loaded samples compared to cell-free carrier samples. All three groups were found to be statistically different from each other in failure torque and stiffness.

Discussion

The results presented here demonstrate that purified, culture-expanded human MSCs are capable of healing a clinically significant bone defect in a well-established model for bone repair. While the osteogenic potential of human MSCs has been proven by neo-osteogenesis in subcutaneous implants (19), as well as in studies of isolated MSCs in vitro (2,23), this is the first demonstration that human MSCs can form bone at an orthotopic site in need of repair. The combination of MSCs with a porous HA/TCP carrier possesses regenerative potential which is histomorphometrically and biomechanically superior to the carrier alone. This investigation paves the way for the clinical application of autologous MSC-therapy for the treatment of orthopedic defects in man.

The progressive increase in radiodensity of the healing bone at 8 weeks parallels the histological observations of processed limbs. Immunocytochemistry proves that the cells associated with the ceramic at 4 weeks are of human origin, and that the cells surrounding the implant are from the host. At 8 weeks and beyond, bone is laid down by the donor MSCs and eventually resorbed and replaced by bone derived from host cells through the normal remodeling sequence (7). It is important to note that in the process of regenerating this osseous defect, bone formation occurs by a direct conversion of mesenchymal cells into osteoblasts rather than by an endochondral cascade. This observation is consistent with previous studies of osteogenesis in implants loaded with animal or human MSCs (18,27,25,68). As the regenerative process continues, the pores of the ceramic are filled with an increasing amount of bone, which is laid down upon the walls of the implant or existing bone, and oriented by the invading vasculature that provides a portal for the entry and establishment of new marrow islands containing hematopoietic elements and host-derived MSCs.

The rate of bone regeneration is lower than that observed in euthymic rats implanted with syngeneic MSCs (25), suggesting that immunocompromised rats are not the ideal hosts to assess the bone-forming potential of human MSCs. This may be due in part to the xenogeneic nature of the implant and the increased natural killer cell activity, which may be a compensatory mechanism for the animal to cope with its deficient T-cell-mediated immunity (49). Nevertheless, a significantly higher amount of bone was formed in the defect which received MSCs compared to those limbs receiving the carrier only. The extent of host-implant union was greater in the MSC-loaded implants, which likely reflects the combined contributions of implanted MSCs and host-derived cells.

The ability of human MSCs to regenerate bone in this experimental model compares favorably with other investigations testing implants such as demineralized bone matrix, bone marrow, purified or recombinant bone morphogenic proteins (BMP), allograft, ceramics, fibermetals and gene-activated matrices. In addition to forming a substantial amount of histologically normal bone, the biomechanical data demonstrate that torsional strength and stiffness at 12 weeks were ~40% that of intact control limbs, which is more than twice that observed with the cell-free carrier, and also twice that achieved in a similar study of bone repair using fresh autograft in a primate long bone defect model (9).

Recently, growth factors such as recombinant human BMP have been implanted in experimental bone defect models in an effort to stimulate bone repair (33,9). Although recombinant BMPs are capable of inducing the endochondral cascade in ectopic implants (57), their ability to reproducibly direct bone formation at orthotopic sites has been hampered by the problems associated with the design and selection of an appropriate carrier. In contrast to the mechanical data showing significant bone regeneration in a MSC-loaded ceramic, BMP delivered in the same HA/TCP carrier did not increase implant strength over the carrier alone (50). The brittle nature of this ceramic, combined with its slow resorption and complex porous structure, may explain why even in the presence of significant bone formation mechanical strength remains less than intact limbs. In addition, stress shielding of the new bone, as a result of the load-bearing fixation plate, also restricts the strength of the healing defect. We believe, as has been previously suggested, that the use of an osteosupportive HA/TCP cylinder may not be the ideal matrix for replacement of diaphyseal defects. Efforts at designing the optimal biomatrix carrier for the delivery of MSCs is an active area of investigation.

Implantation of culture-expanded autologous MSCs offers the advantage of directly delivering the cellular machinery responsible for synthesizing new bone, and circumventing the otherwise slow steps leading to bone repair. Even in patients with a reduced ability to regenerate connective tissue, presumably due to a low titer of endogenous MSCs (28,51,55,1), these rare MSCs may be isolated and culture-expanded over one billion-fold without a loss in their osteogenic potential (3), thus restoring or enhancing a patient's ability to heal tissue defects. The studies presented here suggest that MSC-based cell therapies will be useful for the reconstruction of a variety of tissue defects in man.

EXAMPLE 4

Effect of Coating on the Osteogenic Response of MSC-Loaded HA/TCP Cubes

This experiment was performed in an attempt to establish that uncoated HA/TCP cubes are equivalent to fibronectin- or autologous serum-coated HA/TCP cubes in supporting MSC-mediated osteogenesis.

Materials & Methods

Standard HA/TCP cubes coated with either fibronectin, 1% autologous serum, 10% autologous serum or those left uncoated, were loaded with MSCs and implanted subcutaneously into athymic mice. The cubes were retrieved six weeks post-implantation and inspected for the level of osteogenesis by decalcified histological methods. The experiments were done with multiple human and canine donors, and were performed in duplicate mice.

Results & Conclusion

MSC-loaded cubes from all treatment groups showed a significant amount of bone formation at six weeks. The coating of HA/TCP cubes with either fibronectin or serum had no effect on the level of MSC-mediated osteogenesis within the cube. As expected, the cell-free control HA/TCP cubes did not have osteogenesis. Based on the above results, we conclude that uncoated HA/TCP is a viable carrier for the delivery of MSCs to effect bone repair/augmentation.

EXAMPLE 5

Bone Defect Repair Using Bone Marrow in an Absorbable Gelatin-Containing Sponge The objectives of this study were to demonstrate efficacy of bone marrow and/or mesenchymal stem cells (MSCs) in healing clinically significant bone defects in an established animal model.

Materials & Methods

In the study, Fisher 344 rats (Charles River Laboratories, Wilmington, Mass.) of approximately 325 grams in weight were used. A bilateral femoral gap 8 mm in length was created in each femur. This length is approximately towards the diameter of the mid-diaphysis of the femur. An internal fixation plate was applied with four Kirschner wires. The groups for comparison were separately treated with one of the following:

(1) Gelfoam® sterile sponge (Upjohn—Kalamazoo, Mich.);

(2) Peripheral blood clot plus marrow derived from four bones;

(3) Gelfoam® sponge containing marrow derived from four bones;

(4) Gelfoam® sponge plus varying amounts of marrow from one bone down to one-half of one bone in the presence of fresh peripheral blood to provide clot.

In this animal system, fresh marrow from four bones yields approximately 150 million cells while fresh marrow from one-half of one bone yields approximately 20 million nucleated cells. Each group consisted of a minimum of three animals, all of which were sacrificed six weeks post-operatively to obtain the desired end-points. Some animals received high-resolution Faxitron radiographs at an intermediate point three weeks after implantation. At the six-week time point when all animals were sacrificed, the limbs were removed, radiographed, and prepared for undecalcified histological evaluation.

Handling properties of the Gelfoam® sponge, in combination with fresh marrow in the presence or absence of fresh peripheral blood clot, was desirable and nearly equivalent.

Results

Evaluation of radiographs following sacrifice of the animals at 6 weeks revealed no bone in the defect region of those animals implanted with either Gelfoam® sponge alone or those animals implanted with fresh marrow and a peripheral clot. Minimal endosteal spiking of new bone at the cut edges of the defect was observed, as is the case with the historical control of no implant alone. By contrast, those animals receiving Gelfoam® sponge plus marrow from four bones or one bone, in the absence or presence of peripheral clot, demonstrated a robust osteogenic healing response in the region of the implant. Those animals implanted with Gelfoam® sponge and marrow from one-half of one bone in the presence of peripheral clot respectively demonstrated only modest amounts of bone formation. Finally, those animals implanted with Gelfoam® sponge and marrow from one-half of one bone in the absence of fresh peripheral clot demonstrated no bone in the defect region. Histologic analysis of all of the specimens confirms the observations made based on high-resolution radiographs. The formation of neocortices in samples of Gelfoam® sponge loaded with marrow cells was impressive. Histologic evaluation also indicates that no residual Gelfoam® material was retained at the site of the implant six weeks following surgery. Samples of Gelfoam® sponge loaded with marrow from one bone demonstrated islands of developing hemaetopoietic elements in the medullary canal. Host-implant interfaces appear to be intact.

EXAMPLE 6

Bone Defect Repair in a Canine Model

A 21 mm segmental defect was created in three adult female dogs, and stabilized with a stainless steel orthopaedic plate and screws. The defects were filled with autologous marrow-loaded Gelfoam® sponge. To construct the marrow-loaded sponge, first a piece of Gelfoam® (size 100) sponge (28 mm×21 mm) was hydrated in PBS. Then the sponge was blotted to remove the PBS, folded over and placed into a 10 cc Terumo syringe from which the tip had been cut off. Within five minutes of blotting, 4 cc of freshly aspirated bone marrow from the iliac crest was added to the sponge and allowed to soak into the sponge. After an incubation time of 30–45 minutes to allow clotting of the marrow in the sample, the cylindrical sample was extruded out of the syringe and placed into the defect. The size of the syringe, the dimensions of the sponge, and the marrow volume used was chosen such that the construct aproximated the size and shape of the resected segment.

The dogs were radiographed post-operatively and subsequently every four weeks until sacrifice at sixteen weeks. The femurs containing the implants were harvested at sacrifice and undecalcified histology was performed on the samples.

Figure 10:
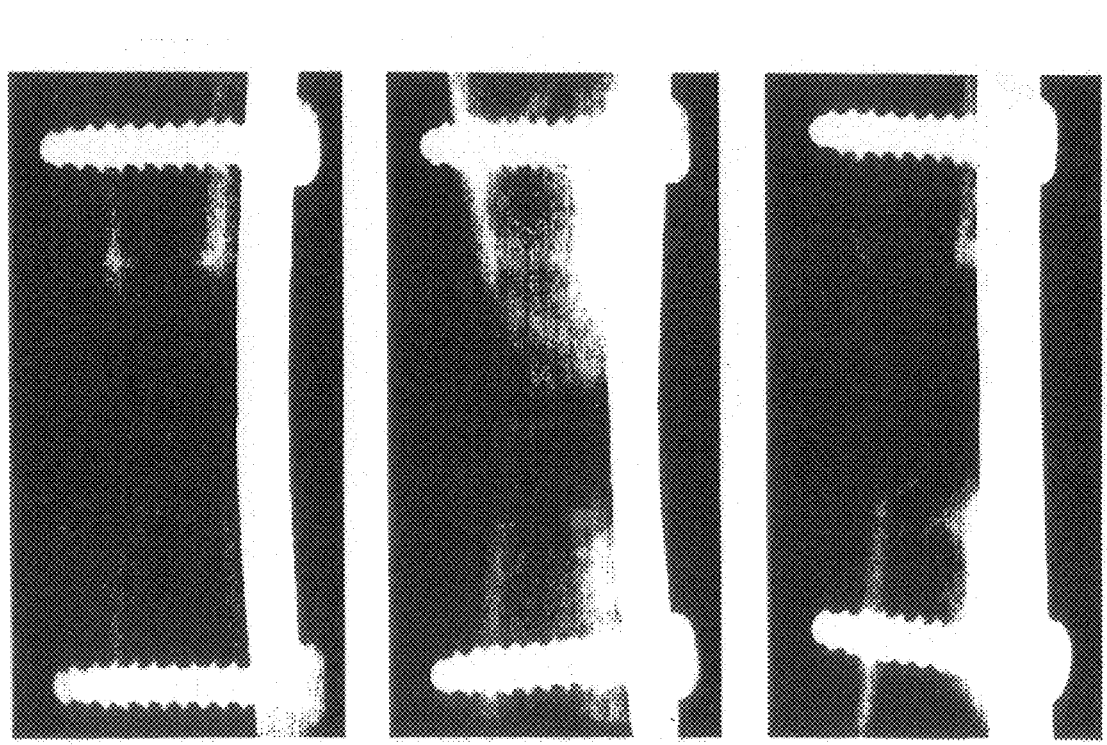
FIG. 10. Radiographic images of a femoral gap in three different canines, 12 weeks post-implantation, with a bone-marrow-loaded gelfoam construct. Substantial amount of mineralized tissue is present in the defect area in all three animals.
Figure 11:
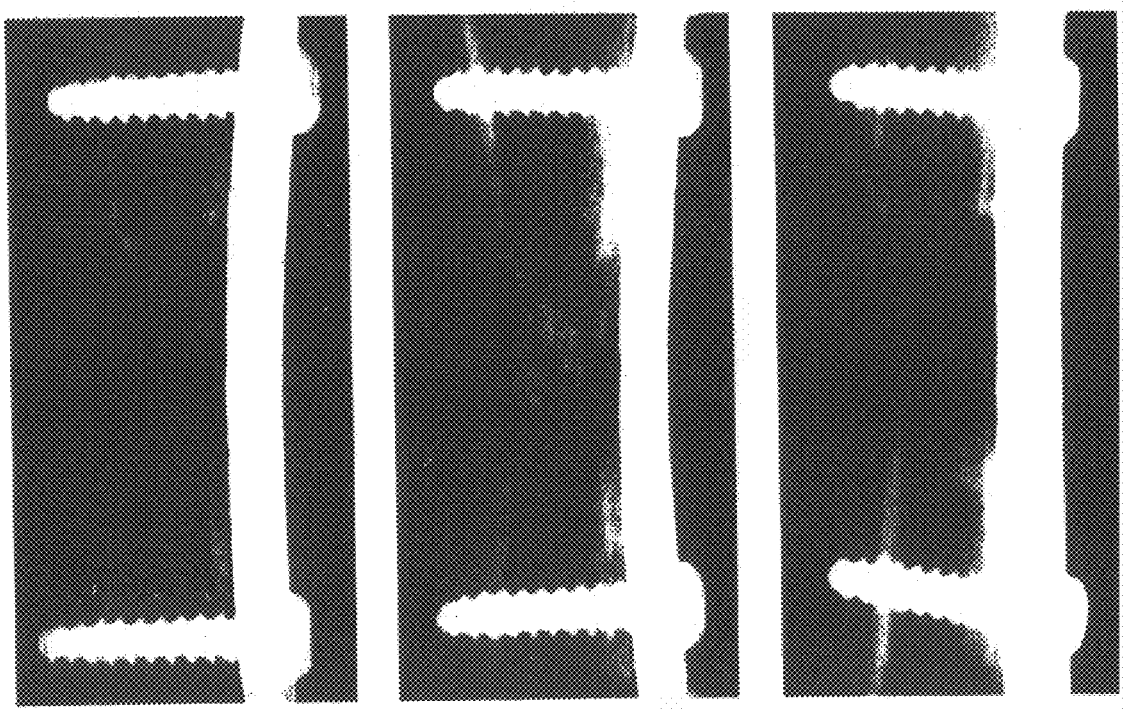
FIG. 11.Radiographic images of a femoral gap in three different canines, 16 weeks post-implantation, with a bone-marrow-loaded gelfoam construct. The bone defect has healed in all three cases and there is a continuous bridge of mineralized tissue spanning the entire defect.

There were no implant failures or other complications with this study. The radiographs were evaluated for healing of the gap and graded according to previously published ordinal scale ranging from 0–4 (Table 6). By 12 weeks, a substantial amount of mineralized tissue was present in the defect area in all three animals (FIG. 10) and by 16 weeks there was a continuous bridge of mineralized tissue spanning the entire defect (FIG. 11). The histologic data confirmed the radiographic conclusions and in all cases the defect was found to have healed by the 16 weeks time point. This was in contrast to defects that had been left empty, which were subsequently found to have only a minimal amount of bone in the defect, and this bone was limited to the regions at the cut edges of the defect. See Johnson et al., J. Orthop. res., 14:351–369, 1996.

TABLE 6

| Dog | Post-Op | 4 weeks | 8 weeks | 12 weeks | 16 weeks |
|-----|---------|---------|---------|----------|----------|
| 3C1 | 0 | 1 | 2 | 4 | 4 |
| 3C2 | 0 | 1 | 2 | 4 | 4 |
| 3C3 | 0 | 1 | 2 | 4 | 4 |

In summary, significant osteogenic response of syngeneic marrow in each of the recipient dogs which were implanted with Gelfoam® sponge indicates the suitability of this cell and matrix combination implantation for the repair of significant bone defects.

Cited Literature

1. Bruder, S. P.; Fink, D. J.; and Caplan, A. I.: Mesenchymal stem cells in bone development, bone repair, and skeletal regeneration therapy. *J. Cell. Biochem.* 56:283–294, 1994.
2. Bruder, S. P.; Eames, B. F.; and Haynesworth, S. E.: Osteogenic induction of purified human mesenchymal stem cells in vitro: Quantitative assessment of the osteoblastic phenotype. *Trans. Ortho. Res. Soc.* 20:464, 1995.
3. Bruder, S. P.; Jaiswal, N.; Haynesworth, S. E.: Growth kinetics, self-renewal and the osteogenic potential of purified human mesenchymal stem cells during extensive subcultivation and following cryopreservation, (1997) *J. Cell Biochem.* 64(2):278–294.
4. Bruder, S. P., Lawrence, E. G., and Haynesworth, S. E. (1995) *Trans. Ortho. Res. Soc.* 20, 8.
5. Bucholz, R. W., Carlton, A., and Holmes, R. E. (1987) *Orthop. Clin. North Am.* 18, 323–334.
6. Caplan, A. I.; Fink, D. J.; Goto, T.; Linton, A. E.; Young, R. G.; Wakitani, S.; Goldberg, V. M.; and Haynesworth, S. E.: Mesenchymal stem cells and tissue repair. In *The Anterior Cruciate Ligament: Current and Future Concepts.* D. W. Jackson, ed. Raven Press, Ltd., New York. 405–417, 1993.
7. Caplan, A. I., and Bruder, S. P. (1997) in *Textbook of Tissue Engineering,* eds. Lanza, R., Langer, R., and Chick, W. (R.G. Landes Company, Georgetown), pp. 603–618.
8. Caplan, A. I. and Pechak, D. (1987) in *Bone and Mineral Research/5,* ed. Peck, W. A. (Elsevier, New York), pp. 117–183.
9. Cook, S. D., Wolfe, M. W., Salkeld, S. L., and Rueger, D. C. (1995) *J. Bone Joint Surg.* 77-A, 734–750.
10. Egrise, D.; Martin, D.; Vienne, A.; Neve, P.; and Schoutens, A.: The number of fibroblastic colonies formed from bone marrow is decreased and the in vitro proliferation rate of trabecular bone cells increased in aged rats. Bone 13:355–361, 1992.
11. Fang, J., Zhu, Y-Y., Smiley, E., Bonadio, J., Rouleau, J. P., Goldstein, S. A., McCauley, L. K., Davidson, B. L., and Roessler, B. J. (1996) *Proc. Natl. Acad. Sci. USA* 93, 5753–5758.
12. Feighan, J. E.; Davy, D.; Prewett, A.; and Stevenson, S: Induction of bone by a demineralized bone matrix gel: a study in a rat femoral defect model. *J. Orthop. Res.* 13:881–891, 1995.
13. Gerhart, T. N.; Kirker-Head, K.; Kriz, M. J.; Holtrop, M. E.; Hennig, G. E.; Hipp, J.; Schelling, S. H.; and Wang, E.: Healing segmental femoral defects in sheep using recombinant human bone morphogenic protein. *Clin. Orthop. Rel. Res.* 293:317–326, 1993.
14. Grande, D. A., Southerland, S. S., Manji, R., Pate, D. W., Schwartz, S. E., and Lucas, P. A. (1995) *Tissue Engin.* 1(4), 345–353.
15. Grundel, R. E.; Chapman, M. W.; Yee, T.; and Moore, D. C.: Autogeneic bone marrow and porous biphasic calcium phosphate ceramic for segmental bone defects in the canine ulna. *Clin. Orthop. Rel. Res.* 266:244–258, 1991.
16. Haynesworth, S. E., Baber, M. A, and Caplan, A. I. (1995) *Trans. Ortho. Res. Soc.* 20, 7.
17. Haynesworth, S. E., Baber, M. A, and Caplan, A. I. (1996) *J. Cell Physiol.* 166(3), 585–592.
18. Haynesworth S E, Baber M A, and Caplan A l.: Cell surface antigens on human marrow-derived mesenchymal cells are detected by monocional antibodies. Bone 13:69–80, 1992.
19. Haynesworth, S. E.; Goshima, J.; Goldberg, V. M.; and Caplan, A. I.: Characterization of cells with osteogenic potential from human marrow. *Bone.* 13:81–88, 1992.

20. Holocek, J.; Lennon, D. L., Haynesworth, S. E.; Marshak, D. R.; and Caplan, A. I: Unpublished data.
21. Hunt, T. R.; Schwappach, J. R.; and Anderson, H. C.: Healing of a segmental defect in the rat femur with use of an extract from a cultured human osteosarcoma cell-line (Saos-2). *J. Bone Joint Surg.* 78(1):41–48, 1996.
22. Jaiswal, N. and Bruder, S. P. Trans. O.R.S.: 524, 1997.
23. Jaiswal, N.; Haynesworth, S. E.; Caplan, A. I.; and Bruder, S. P.: Osteogenic differentiation of purified, culture-expanded human mesenchymal stem cells in vitro, (1997) *J. Cell Biochem.* 64(2):295–312.
24. Johnstone, B.; Yoo, J. U.; Barry, F. P.: in vitro chondrogenesis of bone marrow-derived mesenchymal cells. *Trans. Ortho. Res. Soc.* 21: 65, 1996.
25. Kadiyala, S., Jaiswal, N., and Bruder, S. P. (1997) *Tissue. Engin.* 3, Volume 3, Number 2, 173–185: Culture-expanded, bone marrow-derived mesenchymal stem cells can regenerate a critical-sized segmental bone defect.
26. Kadiyala, S., Kraus, K. H., and Bruder, S. P. (1996) *Trans. Tissue. Engin. Soc.* 1, 20.
27. Kadiyala, S., Young, R. G., Thiede, M. A., and Bruder, S. P. (1997) *Cell Transplant.* 6, Volume 6, Number 2, 125–134: Culture-expanded canine mesenchymal stem cells possess osteochondrogenic potential in vivo and in vitro.
28. Kahn, A.; Gibbons, R.; Perkins, S.; and Gazit, D.: Age-related bone loss: A hypothesis and initial assessment in mice. *Clin. Orthop. Rel. Res.* 313:69–75, 1995.
29. Lane, J. M.; Yasko, A.; Tomin, E.; Bostrom, M.; Rosen, V.; and Wozney, J.: Orthopaedic application of BMP-2 in fracture healing. In *First International Conference on Bone Morphogenic Proteins,* Baltimore, Md., Jun. 8–11 (abstract), 1994.
30. Laurie, S. W. S.; Kaban, L. B.; Mulliken, J. B.; and Murray, J. E.: Donor-site morbidity after harvesting rib and iliac bone. *Plast. Reconstr. Surg.* 73(6):933–938, 1984.
31. Leads from the MMWR. Transmission of HIV through bone transplantation: Case report and publich health recommendations. *JAMA.* 260:2487–2488, 1988.
32. LeBoy, P. S.; Beresford, J.; Devlin, C.; and Owen, M.: Dexamethasone induction of osteoblast mRNAs in rat marrow stromal cell cultures. *J. Cell Physiol.* 146:370–378, 1991.
33. Lee, S. C., Shea, M., Battle, M. A., Kozitza, K., Ron, E., Turek, T., Schaub, R. G., and Hayes, W. C. (1994) *J. Biomed. Mater. Res.* 28, 1149–1156.
34. Lennon, D. P.; Haynesworth, S. E.; Young, R. G.; Dennis, J. E.; and Caplan, A. I.: A chemically defined medium supports in vitro proliferation and maintains the osteochondral potential of rat marrow-derived mesenchymal stem cells. *Exp. Cell Res.* 219:211–222, 1995.
35. Lennon, D. P.; Haynesworth, S. E.; Bruder, S. P.; Jaiswal, N.; and Caplan, A. I.: Human and animal mesenchymal progenitor cells from bone marrow: Identification of serum for optimal selection and proliferation. in vitro Cell. Dev. Biol., 32(10):602–611, 1996.
36. Liang, C. T.; Barnes, J.; Seedor, J. G; Quartuccio, H. A.; Bolander, M.; Jeffrey, J. J.; and Rodan, G. A.: Impaired bone activity in aged rats: Alterations at the cellular and molecular levels. *Bone.* 13:435–441, 1992.
37. Liebergall, M.; Young, R. G.; Ozawa, N.; Reese, J.; Davy, D. T.; Goldberg, V. M.; and Caplan, A. I.: The effects of cellular manipulation and TGF-β in a composite bone graft. In: *Bone Formation and Repair.* Brighton, C., Friedlander, G., and Lane, J. (eds), American Academy of Orthopaedic Surgeons, Rosemont, Ill., 367–378, 1994.
38. Majumdar, M. K.; Haynesworth, S. E.; Thiede, M. A.; Marshak, D. R.; Caplan, A. I.; and Gerson, S. L.: Culture-expanded human mesenchymal stem cells (MSCs) express cytokines and support hematopoiesis in vitro. *Blood* 86(10):494a (1995).
39. Malaval, L.; Modrowski, D.; Ashwani, G.; and Aubin, J. E.: Cellular expression of bone-related proteins during in vitro osteogenesis in rat bone marrow stromal cell cultures. *J. Cell Physiol.* 158:555–572, 1994.
40. Mosca, J. D., Majumdar, M. K., Hardy, W. B., Pittenger, M. F., and Thiede, M. A. (1997) *Blood* 88(10), 186a.
41. Niedzwiedzki, T.; Dabrowski, Z.; Miszta, H.; and Pawlikowski, M.: Bone healing after bone marrow stromal cell transplantation to the bone defect. *Biomaterials* 14:115–121, 1993.
42. Ou Y, Piedmonte M R, and Medendrop S V.: Latent variable models for clustered ordinal data. Submitted to Biometrics.
43. Owen, M.; Lineage of osteogenic cells and their relationship to the stromal system. In *Bone and Mineral/3.* W. A. Peck, ed. Elsevier, Amsterdam, 1–25, 1985.
44. Owen, M.: Marrow stromal stem cells. *J. Cell Sci. Suppl.* 10:63–76, 1988.
45. Pereira, R. F.; Halford, K. W.; O'Hara, M. D.; Leeper, D. B.; Sokolov, B. P.; Pollard, M. D.; Bagasra, O.; and Prockop, D. J.: Culture adherent cells from marrow can serve as long-lasting precursor cells for bone, cartilage, and lung in irradiated mice. *Proc. Natl. Acad. Sci. USA.* 92:4857–4861, 1988.
46. Pittenger, M. F., Mackay, A. M., and Beck, S. C. (1996) *Mol. Biol. Cell.* 7, 582a.
47. Quarto, R.; Thomas, D.; and Liang, T.: Bone progenitor cell deficits and the age-associated decline in bone repair capacity. *Calcif. Tissue Int.* 56:123–129, 1995.
48. Saito, T.; Dennis, J. E.; Lennon, D. P.; Young, R. G.; and Caplan, A. I.: Myogenic expression of mesenchymal stem cells within myotubes of mdx mice in vitro and in vivo. *Tissue. Engin.* 1(4):327–343, 1995.
49. Schuurman, H.-J., Hougen, H. P., and van Loveren, H. (1992) *ILAR Journal.* 34(1–2), 3–12.
50. Stevenson, S.; Cunningham, N.; Toth, J.; Davy, D.; and Reddi, A. H.: The effect of osteogenin (a bone morphogenic protein) on the formation of bone in orthotopic segmental defects in rats. *J. Bone Joint Surg.* 76(11): 1676–1687. 1994.
51. Tabuchi, C.; Simmon, D. J.; Fausto, A.; Russell, J.; Binderman, I.; and Avioli, L.: Bone deficit in ovariectomized rats. *J. Clin. Invest.* 78:637–642, 1986.
52. Tsuji, T.; Hughhes, F. J.; McCulloch, C. A.; and Melchher, A. H.: Effect of donor age on osteogenic cells of rat bone marrow in vitro. *Mech. Ageing Dev.* 51:121–132, 1990.
53. Wakitani, S.; Gotto, T.; Pineda, S. J.; Young, R. G.; Mansour, J. M.; Caplan, A. I.; and Goldberg, V. M.: Mesenchymal cell-based repair of large, full-thickness defects of articular cartilage *J. Bone Joint Surg.* 76A:579–592, 1994.
54. Wakitani, S.; Saito, T.; and Caplan, A. I.: Myogenic cells derived from rat bone marrow mesenchymal stem cells exposed to 5-azacytidine. *Muscle & Nerve* 18:1417–1426, 1995.
55. Werntz, J. R.; Lane, J. M.; Burstein, A. H.; Justin, R.; Klein, R.; and Tomin, E.: Qualitative and quantitative analysis of orthotopic bone regeneration by marrow. *J. Orthop. Res.* 14:85–93, 1996.
56. Wolff, D.; Goldberg, V. M.; and Stevenson, S.: Histomorphometric analysis of the repair of a segmental diaphyseal defect with ceramic and titanium fibermetal implants: Effects of bone marrow. J. Orthop. Res. 12:439-446, 1994.

57. Wozney, J. M.; Rosen, V.; Celeste, A. J.; Mitsock, L. M.; Whitters, M. J.; Kriz, R. W.; Hewick, R. M.; and Wang, E. A.: Novel regulators of bone formation: Molecular clones and activities. *Science.* 242:1528–1534, 1988.
58. Young, R. G., Butler, D. L., Weber, W., Gordon, S. L., and Fink, D. J. (1997) *Trans. Ortho. Res. Soc.* 22, 249.

What is claimed is:

1. A method of augmenting bone formation in an individual in need thereof by administering to said individual isolated human mesenchymal stem cells with a resorbable biopolymer selected from the group consisting of a gelatin, collagen, and cellulose, wherein said resorbable biopolymer supports the differentiation of such stem cells into the osteogenic lineage to an extent sufficient to generate bone formation therefrom.

2. A composition for augmenting bone formation, said composition comprising a resorbable biopolymer selected from the group consisting of gelatin, cellulose, and collagen, in combination with isolated mesenchymal stem cells.

3. A composition for augmenting bone formation, said composition comprising a resorbable biopolymer selected from the group consisting of gelatin, cellulose, and collagen, wherein said resorbable biopolymer is a sponge, strip, film, gel, or web, or a structurally stable, three dimensional implant, in combination with isolated mesenchymal stem cells.

4. A method for augmenting bone formation in an individual in need thereof which comprises administering to said individual a composition comprising a resorbable biopolymer selected from the group consisting of gelatin, cellulose, and collagen in combination with isolated mesenchymal stem cells.

5. The method of claim 1 wherein the medium is a powder, sponge, strip, film, gel or web or a structurally stable, three dimensional implant in the form of a cube, cylinder or block or in the shape of an anatomical form.

6. The method of claim 1 wherein the resorbable biopolymer is a porcine skin-derived gelatin.

7. The method of claim 1 which further comprises administering to said individual at least one bioactive factor which induces or accelerates the differentiation of such mesenchymal stem cells into the osteogenic lineage.

8. The method of claim 7 wherein the cells are contacted with the bioactive factor ex vivo.

9. The method of claim 8 wherein the cells are contacted with the bioactive factor when in contact with the matrix which supports the differentiation of such stem cells into the osteogenic lineage to an extent sufficient to generate bone formation therefrom.

10. The method of claim 7 wherein the bioactive factor is a synthetic glucocorticoid.

11. The method of claim 10 wherein the synthetic glucocorticoid is dexamethasone.

12. The method of claim 7 wherein the bioactive factor is a bone morphogenic protein.

13. The method of claim 12 wherein the bone morphogenic protein is in a liquid or semi-solid carrier suitable for intramuscular, intravenous, intramedullary or intra-articular injection.

14. The method of claim 12 wherein the bone morphogenic protein is selected from the group consisting of BMP-2, BMP-3, BMP4, BMP-6 and BMP-7.

15. A method for augmenting bone formation in an individual in need thereof which comprises administering to said individual thereof a bone formation augmenting amount of the composition of claim 2.

16. A method for augmenting bone formation in an individual in need thereof which comprises administering to said individual thereof a bone formation augmenting amount of the composition of claim 3.

* * * * *